(12) United States Patent
Kimura et al.

(10) Patent No.: US 6,566,094 B1
(45) Date of Patent: May 20, 2003

(54) SEMAPHORIN GENE: SEMAPHORIN Y

(75) Inventors: Toru Kimura, Kusatsu; Kaoru Kikuchi, Takarazuka, both of (JP)

(73) Assignee: Sumitomo Pharmaceuticals Company, Limited, Osaka-fu (JP)

( * ) Notice: Subject to any disclaimer, the term of this patent is extended or adjusted under 35 U.S.C. 154(b) by 0 days.

(21) Appl. No.: 09/254,594

(22) PCT Filed: Sep. 9, 1997

(86) PCT No.: PCT/JP97/03167

§ 371 (c)(1),
(2), (4) Date: May 11, 1999

(87) PCT Pub. No.: WO98/11216

PCT Pub. Date: Mar. 19, 1998

(30) Foreign Application Priority Data

Sep. 11, 1996 (JP) .............................................. 8-263565
Aug. 8, 1997 (JP) .............................................. 9-227220

(51) Int. Cl.$^7$ ........................ C07H 21/04; C12N 15/00; C12N 5/00; C12N 15/63; C12P 21/06
(52) U.S. Cl. .................... 435/69.1; 435/70.1; 435/71.1; 435/252.1; 435/252.3; 435/320.1; 435/325; 435/440; 435/455; 536/23.1; 536/23.5
(58) Field of Search .............................. 536/23.5, 23.1; 435/325, 252.1, 252.3, 440, 455, 320.1, 69.1, 70.1, 71.1

(56) References Cited

U.S. PATENT DOCUMENTS

| | | | |
|---|---|---|---|
| 5,416,197 A | 5/1995 | Raper et al. | |
| 5,639,856 A | * 6/1997 | Goodman et al. | .......... 530/326 |
| 5,684,133 A | 11/1997 | Schwab et al. | |
| 5,807,826 A | 9/1998 | Goodman et al. | |
| 5,807,862 A | 9/1998 | Klein et al. | |
| 5,935,865 A | 8/1999 | Goodman et al. | |

FOREIGN PATENT DOCUMENTS

| | | |
|---|---|---|
| EP | 0 121 338 | * 10/1984 |
| EP | 0396719 B1 | 11/1990 |
| WO | WO 9417831 | 8/1994 |
| WO | WO 9507706 | 3/1995 |
| WO | 97/20928 | 6/1997 |

OTHER PUBLICATIONS

Kolodkin et al. GenBank Accession No. L26082, Feb. 20, 1996.*
Hillier et al. GenBank Accession No. R59527, May 24, 1995.*
Hillier et al. GenBank Accession No. T82101, Mar. 15, 1995.*
Matthes et al., Cell, vol. 81, 631–639 (1995).
Messersmith et al., Neuron, vol. 14, 949–959 (1995).
Clifford J. Woolf, Nature, vol. 378, 439–440 (1995).
Eckhardt et al., Molecular and Cellular Neuroscience 9, 409–419 (1997).
Koppel, Neuron, vol. 19, 531–537 (1997).
Furuyama et al., The Journal of Biological Chemistry, vol. 271, No. 52, 33376–33381 (1996).
Mangasser–Stephan et al., Bichemical and Biophysical Research Communications 234, 153–156 (1997).
Herold et al., The Journal of Immunology, "CD100 Is Associated with CD 45 at the Surfce of Human T Lymphocytes," 5262–5268 (1996).
Schwab et al, Annu. Rev. Neurosci 16, 565–595 (1993).
Richardson et al., Nature, vol. 284, 264–265 (1980).
David et al., Science, vol. 214, 931–933 (1981).
Schnell et al., Nature, vol. 343, 269–272 (1990).
Luo et al., Cell, vol. 75, 217–227 (1993).
Bregman et al., Nature, vol. 378, 498–501 (1995).
Dodd et al, Cell, vol. 81, 471–474 (1995).
Kolodkin et al., Neuron, vol. 9, 831–845 (1992).
Schwab et al., The Journal of Neuroscience 8(7), 2381–2393 (1988).
Bandtlow et al., Science, vol. 259, 80–83 (1993).
Luo et al., Neuron, vol. 14, 1131–1140 (1995).
GenBank, Accession No. R59527, Created May 24, 1995.
Alan R. Johnson, BioEssays, vol. 15, No. 12, 807–813 (1993).
Genome Research, 1, 35–42 (1996), G. Lanfranchi et al.
Cell, vol. 75, 1389–1399 (1993), Alex L. Kolodkin et al.
Neuron, vol. 14, 941–948 (1995) Andreas W. Puachel et al.
Molecular and Cellular Neuroscience, 9, 26–41 (1997), L. Zhou et al.
Adams et al., "A novel class of murine semaphorins with homology to thrombospondin is differentially expressed during early embryogenesis", Mechanisms of Development, Elsevier Science Ireland Ltd. IE., vol. 57, Jun. 1996, pp. 33–45, XP000926255.
Culotti et al., "Functions of netrins and semaphorins in axon guidance", Current Opinion in Neurobiology, London, GB., vol. 6, No. 1, Feb. 1, 1996, pp. 81–88, XP002084498.

* cited by examiner

*Primary Examiner*—Anne-Marie Baker
(74) *Attorney, Agent, or Firm*—Birch, Stewart, Kolasch & Birch, LLP

(57) ABSTRACT

Semaphorin Y inhibiting neurite outgrowth, and a nucleotide sequence therefor, as well as other Semaphorin sequences hybridizing to the Semaphorin Y sequence, modified proteins or partial peptides of Semaphorin Y, antibodies against Semaphorin Y, antisense nucleotides against Semaphorin Y gene, and the use of such substances as pharmaceutical or diagnostic agents or laboratory reagents are disclosed. Further, a method of screening for Semaphorin Y antagonists employing Semaphorin Y, Semaphorin Y antagonists obtained by the screening method, pharmaceutical agents comprising such antagonists, and transgenic animals involving Semaphorin Y are also disclosed.

7 Claims, 5 Drawing Sheets

SEMAPHORIN GENE: SEMAPHORIN Y

This application is the national phase under 35 U.S.C. §371 of prior PCT International Application No. PCT/JP97/03167 which has an international filing date of Sep. 9, 1997 which designated the United States of America.

TECHNICAL FIELD

The present invention relates to Semaphorin Y, a novel Semaphorin belonging to the Semaphorin family, and use of Semaphorin Y for pharmaceutical or diagnostic agents or laboratory reagents. More particularly, it relates to Semaphorin Y inhibiting neurite outgrowth, and a gene therefor, as well as other Semaphorins hybridizing to said Semaphorin Y gene, modified proteins or partial peptides of said Semaphorin Y, antibodies against said Semaphorin Y, antisense nucleotides against said Semaphorin Y gene, antagonists of said Semaphorin Y, transgenic animals, and their use as pharmaceutical or diagnostic agents or laboratory reagents.

BACKGROUND ART

It is widely known that a central nervous system (CNS)-neuron in higher organisms such as human is not capable of regeneration once injured. Therefore, one who has received an injury on his (her) spinal cord due to, for example, a traffic accident, is compelled to spend the rest of his (her) life in a hemiplegic state. On the contrary, it is known that a peripheral nervous system (PNS)-neuron retains a vigorous regeneration ability even in those higher organisms, and therefore, neurons in a limb, when disconnected, can gradually regenerate with a concomitant recovery of their function.

In the early nineteen eighties, a group of Aguayo et al. found that when PNS-neuron is experimentally grafted into an injured CNS-neuron in a higher organism, axon growth of CNS-neuron is induced. This observation demonstrates that CNS-neuron in higher organisms which had been generally considered not to have a regeneration ability can regenerate if a suitable environment is provided (*Nature,* 284, 264–265 (1980), *Science,* 214, 931–933 (1981)). That report suggests a possibility that in CNS of higher organisms, there may exist a factor, namable "CNS-neuron regeneration inhibitor", which inhibits the regeneration of CNS-neuron, and that a release from such inhibition may allow the regeneration of CNS-neurons. This suggestion paved the way for a CNS-neuron regeneration therapy.

In 1988, a group of Schwab et al. demonstrated that there exited such CNS-neuron regeneration inhibitor among proteins derived from CNS myelin. They also succeeded in purifying, though partially, a protein having said CNS-neuron regeneration inhibition activity, and named this protein fraction NI35/250 (*Annu. Rev. Neurosci.,* 16, 565–595 (1993)), although no one has succeeded in its isolation, identification and gene cloning yet. In addition, they immunized animals with the partial purified NI35/250, and succeeded in obtaining an antibody (IN-1) having a neutralizing activity. This antibody is capable of recognizing a band for NI35/250 in Western blotting, and capable of staining, in an immunostaining, the region to which NI35/250 is supposed to be distributed. Furthermore, they demonstrated that administration of this antibody to an animal experimentally received an injury on its spinal cord has promoted regeneration of axons in spinal cord, though partially, within 2–3 weeks, and restored its function within 2–3 months (*Nature,* 343, 269–272 (1990), *Nature,* 378, 498–501 (1995)). These findings are of great value, because they experimentally demonstrated that there existed a CNS-neuron regeneration inhibitor as suggested by Aguayo et al. (supra) and that CNS-neuron can be regenerated by inhibiting the activity of said inhibitor. The above antibody is, however, directed not to human but to rat NI35/250, and exhibits a low stability and specificity. In addition, although regeneration of CNS-neuron was observed as described above by administering said antibody, its effect was so partial and incomplete that not all of the motor functions could be restored. It is, therefore, believed essential in solving these problems to identify the gene for NI35/250 or corresponding CNS-neuron regeneration inhibitor, and, based on knowledges of molecular biology, neuroscience and the like, develop an antagonist more effectively inhibiting the CNS-neuron regeneration inhibition activity, or develop a method for inhibiting the expression of the gene for said regeneration inhibitor.

Apart from the above, the nervous system, whether it is central or peripheral, requires formation of a complicated neural network among neurons or between neurons and peripheral receivers or effectors during development, that is, in the stage of embryo or fetus, in order to precisely carry out its principal functions, i.e., to transfer and process the information. To establish the neural network, an ingenious mechanism is necessary, which precisely guides a growing neurite to the target site locating remote therefrom.

It has been hitherto believed that a factor which positively controls the neurite outgrowth, such as neurite growth promoter and neurite growth attractant may play a major role in the formation of the neural network. However, it is now being demonstrated by recent studies on the mechanism of the network formation that the opposite factor, that is, a negative factor having an outgrowth inhibition activity is important for an accurate guidance (*Cell,* 78, 353–356 (1994)).

A representative factor having such an outgrowth inhibition activity is a protein called "Semaphorin". Semaphorin firstly discovered is Fasciclin IV found in grasshopper. Collapsin (latterly named Collapsin I) was subsequently discovered in chick (*Cell,* 75, 217–227 (1993); *Neuron,* 9, 831–845 (1992)). To date, more than 10 genes belonging to the Semaphorin family have been reported in a wide range of species covering insects such as drosophila and beetle, human, and viruses (*Cell,* 81, 471–474 (1995)). These Semaphorins characteristically contain in their amino acid sequences similar structures called semaphorin domains each consisting of about 500 amino acids (*Neuron,* 14, 941–948 (1995); *Cell,* 75, 1389–1399 (1993)). However, the homologies of the primary amino acid sequences in semaphorin domains among these Semaphorin genes are 80–20%, and not necessarily high.

Of these Semaphorins, functions have been verified for only a few, including, for example, Fasciclin IV of grasshopper, Semaphorins I and II of drosophila, Collapsin of chick, and Semaphorin III which corresponds to Collapsin in mammals. All of these Semaphorins are known to inhibit neurite outgrowth or synapsis formation. In particular, Semaphorin III has been reported to have an activity collapsing in a short time the growth cone of cultured neuron (growth-cone collapse activity) in vitro (*Neuron,* 14, 941–948 (1995); *Neuron,* 14, 949–959 (1995); *Cell,* 81, 631–639 (1995); *Cell,* 75, 1389–1399 (1993); *Cell,* 14, 217–227 (1993); *Neuron,* 9, 831–845 (1992)).

Although it is now being demonstrated, as described above, that known Semaphorins have a growth-cone collapse activity and a neurite outgrowth inhibition activity during development, and play a role in giving an accurate guidance to neuron, it is not evident at present whether or not their Semaphorins exert some function not only during development but also in the adult, and less evident whether or not Semaphorins play a role as a CNS-neuron regeneration inhibitor. Of course, since known Semaphorins have been shown to be a negative guidance factor inhibiting neurite outgrowth, it would not be unreasonable to consider said Semaphorins as a candidate for a CNS-neuron regeneration inhibitor (*Nature*, 378, 439–440 (1995)). However, it has been shown by in vitro experiments that Semaphorin III (Sema III), only one Semaphorin of higher organisms of which function has been analyzed, exerts its neurite-outgrowth inhibition activity on a sensory neuron and sympathetic neuron both of which are peripheral, but not on a retinal neuron which is central (*Cell*, 75, 217–227 (1993)). In addition, Northern analysis on the distribution of Sema III expression in the adult conducted by the present inventors has revealed that it is expressed mainly in peripheral tissues (see Reference example 2 below). It is therefore hardly believed that Sema III having such features has a function as a CNS-neuron regenen inhibitor.

Problem to be Solved by the Invention

The present invention aims to provide Semaphorin Y, a novel Semaphorin belonging to the Semaphorin family, and a gene therefor, and to provide pharmaceutical agents for neural diseases, in particular for regeneration of CNS-neuron, and related diagnostic agents or laboratory reagents. More specifically, the present invention aims to provide Semaphorin Y inhibiting neurite outgrowth and a gene therefor, as well as other Semaphorins hybridizing to said Semaphorin Y gene, modified proteins or partial peptides of said Semaphorin Y, antibodies against said Semaphorin Y, antisense nucleotides against said Semaphorin Y gene, and use of such substances as pharmaceutical or diagnostic agents or laboratory reagents. The present invention further aims to provide a method of screening for Semaphorin Y antagonists empolying said Semaphorin Y, Semaphorin Y antagonists obtained by said screening method, pharmaceutical agents comprising such antagonists, and transgenic animals involving Semaphorin Y.

Means of Solving the Problem

In order to provide pharmaceutical agents for neural diseases, in particular for regeneration of CNS-neuron, and related diagnostic agents or laboratory reagents, the present inventors have planed to identify a novel Semaphorin which has not yet been cloned. In particular, the present inventors have paid their attention to the similarity between the in vitro activities of the above-described NI35/250 and Semaphorin, i.e., to the fact that NI35/250 has a growth-cone collapse activity and a neurite-growth inhibition activity in vitro (*J. Neurosci.*, 8, 2381–2393 (1988); *Science*, 259, 80 (1993)), while known Semaphorins similarly possess a neurite-growth inhibition activity, and particularly Semaphorin III has also a growth-cone collapse activity. This suggested to the inventors the possibility that unknown Semaphorins which have not yet been identified may include the one inhibiting regeneration of CNS-neuron. Specifically, the present inventors' idea was that Semaphorin, which is characterized in that 1) it is widely expressed throughout the CNS of adult where regeneration of neuron (or neurite outgrowth) is inhibited, but 2) it is poorly expressed in other tissues such as peripheral tissues in the adult, has not been identified yet, and if one can identify a new unknown Semaphorin having such characteristics, the Semaphorin might be involved in inhibition of regeneration of CNS-neuron.

First of all, the inventors have closely searched DNA database on the basis of the amino acids sequence relatively well conserved among previously reported Semaphorin genes. Specifically, a DNA sequence has been searched through EST (Expressed Sequence Tags) database, which is a gene not expressed in peripheral tissues but expressed in the postnatal brain and which encodes an amino acid sequence relatively well conserved among Semaphorins. As a consequence, a DNA fragment R59527 (referred to in the sequence listing as SEQ ID NO: 12, here and after referred to as "R59527") was identified, which encodes, as a partial sequence, a sequence consisting of seven amino acids: Gln (or Arg)-Asp-Pro-Tyr-Cys-Ala (or Gly)-Trp (SEQ ID NO: 12). The R59527 gave a sequence information as to only 238 bases, and furthermore only several percent thereof could be translated into an amino acid sequence common to those of known Semaphorins. In addition, the reading frame could not be determined because of the presence of sequence not definitely determined in R59527. It was, therefore, utterly impossible at that stage to conclude that the base sequence of R59527 is part of a novel Semaphorin. We have, however, finally succeeded in cloning a novel Semaphorin gene by carrying out the following procedures: synthesizing DNA primers on the basis of that sequence information; conducting PCR with said primers using cDNAs prepared from a human hippocampal cDNA library as templates to obtain a novel DNA fragment (SEQ ID NO: 7) consisting of 170 bases; labeling the DNA fragment with $^{32}$P to synthesize a DNA probe; and screening rat and human cDNA libraries with that probe. We named this novel Semaphorin "Semaphorin Y".

Subsequent analysis revealed that Semaphorin Y is a novel Semaphorin at which we aimed, since it was widely expressed in CNS in the adult, whereas among peripheral tissues the expression could be observed only in limited tissues.

Semaphorin Y of the present invention having such characteristics appears to be involved in inhibition of regeneration of CNS-neuron in the adult. Semaphorin Y may be used to screen for Semaphorin Y antagonists, and antagonists identified in such screening system are expected to promote regeneration of CNS-neuron. Similarly, antisense DNAs or RNAs against Semaphorin Y gene are also expected to promote regeneration of CNS-neuron as the above antagonists do.

In addition, in view of the fact that Semaphorin Y of the present invention inhibits neurite outgrowth, it may be used as a therapeutic or diagnostic agent for pains or immune diseases such as atopic dermatitis, by administering it to peripheral tissues, which results in the inhibition of neurite outgrowth of PNS-neuron. Furthermore, Semaphorin Y is a novel Semaphorin belonging to the Semaphorin family of which expression distribution is unconventionally characteristic as described above, and also has a characteristic in that it does not contain any Ig domains commonly found among hitherto reported Semaphorins of vertebrates. Semaphorin Y may, therefore, serve as an important research material or a laboratory reagent.

The present invention has been completed on the basis of the above findings.

Thus, the gist of the present invention is as follows:
(1) a gene encoding the following protein (a) or (b):
  (a) Semaphorin Y protein comprising the amino acid sequence shown in SEQ ID NO: 3 or 6,
  (b) a protein which comprises an amino acid sequence wherein one or more amino acids are deleted, substituted and/or added in the amino acid sequence shown in SEQ ID NO: 3 or 6, and which protein inhibits neurite outgrowth;
(2) a gene comprising the following DNA (a) or (b):
  (a) Semaphorin Y DNA comprising the base sequence shown in SEQ ID NO: 1, 2, 4, or 5,
  (b) DNA which hybridizes under stringent conditions to DNA comprising the base sequence shown in SEQ ID NO: 1, 2, 4, or 5, and which encodes a protein inhibiting neurite outgrowth;
(3) a gene comprising DNA which hybridizes under stringent conditions to DNA comprising the base sequence shown in SEQ ID NO: 7, and which encodes a protein having a semaphorin domain;
(4) a protein obtained by expressing the gene of any one of the above items (1) to (3);
(5) a gene comprising DNA which encodes a protein comprising an amino acid sequence in which one or more amino acids are deleted, substituted and/or added in the protein shown in SEQ ID NO: 3 or 6, wherein said protein promotes neurite outgrowth;
(6) a protein obtained by expressing the gene of the above item (5);
(7) DNA which is cloned from a human cDNA library or a human genomic library, and which hybridizes under stringent conditions to DNA comprising at least part of DNA consisting of the base sequence shown in SEQ ID NO: 1 or 4;
(8) an expression plasmid which expresses either the gene of any one of the above items (1) to (3) and (5), or DNA of the above item (7);
(9) a transformant transformed with the expression plasmid of the above item (8);
(10) a process for producing a recombinant protein, which process comprises culturing the transformant of the above item (9), and recovering the recombinant protein expressed;
(11) a peptide comprising at least six amino acids of the protein of the above item (4) or (6);
(12) a peptide of the above item (11) which promotes neurite outgrowth;
(13) a peptide of the above item (11) characterized in that it contains aspartic acid residue at position 198 of the amino acid sequence shown in SEQ ID NO: 6 or an amino acid residue corresponding to the position of said aspartic acid residue;
(14) an antisense nucleotide, or chemically modified variant thereof, which is directed against a segment comprising at least eight or more bases in the gene of any one of the above items (1) to (3), or in DNA of the above item (7);
(15) an antisense nucleotide or chemically modified variant thereof of the above item (14), characterized in that it inhibits expression of the protein of the above item (4);
(16) an antibody against the protein of the above item (4) or (6), or against the peptide of any one of the above items (11) to (13);
(17) a pharmaceutical agent comprising, as an active ingredient, the gene of any one of the above items (1) to (3) and (5), DNA of the above item (7), the protein of the above item (4) or (6), the peptide of any one of the above items (11) to (13), the antisense nucleotide or chemically modified variant thereof of the above item (14) or (15), or the antibody of the above item (16);
(18) a method of screening for Semaphorin Y antagonists, characterized in that it employs the protein of the above item (4);
(19) Semaphorin Y antagonist obtained by the screening method of the above item (18);
(20) Semaphorin Y antagonist of the above item (19) which comprises the protein of the above item (6), the peptide of any one of the above items (11) to (13), or the antibody of the above item (16);
(21) a CNS-neuron regeneration promoter, characterized in that it contains at least one of the antisense nucleotides or chemically modified variants thereof of the above item (14) or (15), or Semaphorin Y antagonists of the above item (19) or (20);
(22) a neurite outgrowth inhibitor for PNS-neuron, characterized in that it contains at least one of the proteins of the above item (4); and
(23) a transgenic animal in which either the gene of any one of the above items (1) to (3) and (5), or DNA of the above item (7) has been artificially inserted into its chromosome, or has been knocked out.

Mode for Carrying Out the Invention

The 1st embodiment of the present invention is a gene which encodes Semaphorin Y comprising the amino acid sequence shown in SEQ ID NO: 3 or 6, or a gene encoding a protein which comprises an amino acid sequence wherein one or more amino acids are deleted, substituted and/or added in the amino acid sequence of the above Semaphorin Y, and which protein inhibits neurite outgrowth. The 2nd embodiment of the present invention is Semaphorin Y gene comprising the base sequence shown in SEQ ID NO: 1, 2, 4, or 5, or a gene which hybridizes under stringent conditions to such Semaphorin Y gene and which encodes a protein inhibiting neurite outgrowth. These genes are explained below in order.

1) Gene Encoding Semaphorin Y (Semaphorin Y Gene)

Of the above-mentioned genes, "a gene which encodes Semaphorin Y protein comprising the amino acid sequence shown in SEQ ID NO: 3" or "Semaphorin Y gene comprising the base sequence shown in SEQ ID NO: 1 or 2" is a gene encoding the rat Semaphorin Y of the present invention, while "a gene which encodes Semaphorin Y protein comprising the amino acid sequence shown in SEQ ID NO: 6" or "Semaphorin Y gene comprising the base sequence shown in SEQ ID NO: 4 or 5" is a gene encoding the human Semaphorin Y of the present invention. Among these genes, those shown in SEQ ID NOs: 2 and 5 correspond open reading frames for rat and human types of Semaphorin Y, respectively. Such genes may be cloned, as described in Example 1, by screening a cDNA library derived from CNS tissues using a probe (for example, a DNA probe having the base sequence shown in SEQ ID NO: 7) prepared on the basis of the sequence of "R59527" found in EST database. Particular techniques for such cloning may be found in the standard texts such as "Molecular Cloning, 2nd ed.", Cold Spring Harbor Laboratory Press (1989). The base sequence of the cloned DNA may also be determined by conventional methods, for example, using a sequencing kit commercially available.

Alternatively, after publication of the base sequence of rat and human Semaphorin Y cDNAs of the present invention, one skilled in the art can also easily clone the full-length genes encoding rat and human types of Semaphorin Y by using part of said cDNA as a probe, without using cloning methods as described above.

2) Gene Encoding Modified Protein of Semaphorin Y

Of the above-mentioned genes, "a gene encoding a protein which comprises an amino acid sequence wherein one or more amino acids are deleted, substituted and/or added in the amino acid sequence of the above Semaphorin Y, and which protein inhibits neurite outgrowth" refers to a gene encoding a so-called "modified proteins" of Semaphorin Y which inhibits neurite outgrowth. Those skilled in the art may easily obtain a gene encoding such protein, for example, by site-directed mutagenesis (*Methods in Enzymology*, 100, 448- (1983)) or PCR method (*Molecular Cloning*, 2nd ed., Chapter 15, Cold Harbor Laboratory Press (1989); "PCR A Practical Approach", IRL Press, 200–210 (1991)). In this context, the number of amino acid residues to be deleted, substituted and/or added is to be such a number that permits the deletion, substitution and/or addition by well-known methods such as site-directed mutagenesis described above.

For the purpose of the present invention, the phrase "inhibiting neurite outgrowth" means that the protein has the collapse activity on growth cone of neuron, or that the protein has the neurite-outgrowth inhibition activity. These activities may be measured with a test substance such as an expression product of DNA encoding Semaphorin Y or modified protein thereof, for example, in the following manner:

Since Semaphorin Y is a membrane protein, it exists in the cell membrane of the cells transformed with Semaphorin Y gene. The activities of the above test substance may, therefore, easily be measured by using, as a test material, the membrane fraction of the transformed cells.

Examples of activity measurement include measurement of collapse activity on growth cone of neuron (M. Igarashi et al., *Science*, vol. 259, pp. 77–79 (1993)), or measurement of neurite-outgrowth inhibition activity (e.g., J. A. Davies et al., *Neuron*, vol. 2, pp. 11–20 (1990) and M. Bastmeyer, *J. Neurosci.*, vol. 11, pp. 626–640 (1991)). A method of measuring the growth-cone collapse activity is described in detail in literature (M. Igarashi et al., *Science*, vol. 259, pp. 77–79 (1993)). Briefly, the measurement may be carried out by a method in which cells expressing a test substance such as Semaphorin Y is homogenized, and the homogenate containing the cell membrane fraction or the purified membrane fraction is used (E. C. Cox et al., *Neuron, vol.* 2, pp. 31–37 (1990)), or by a method in which a protein extracted from the membrane fraction is reconstituted in a liposome and the liposome is used as a test material (C. E. Bandtlow, *Science*, vol. 259, pp. 80–84 (1993)). In order to measure the growth-cone collapse activity in practice using these materials, a test substance such as Semaphorin Y, for example, in one of the forms as describe above is added to neurons cultured under conventional conditions (e.g., "Culturing, Nerve Cells" edited by Banker et al., MIT Press (1991)) in a container coated with a substance promoting the neurite outgrowth and the growth-cone formation such as laminin, collagen, polylysine or polyornithine. After the addition, when a sufficient time has passed to occur collapse of growth cone (typically from 30 minutes to one hour after the addition), those neurons are fixed with 1% glutaraldehyde or the like, and the number of the growth cones which have been collapsed is counted under a microscope. In this measurement, it is important that another sample is used as a control, which is prepared from cells not expressing the test substance such as Semaphorin Y according to the completely same procedures as those used for the test substance-expressing cells. Typically, normalization of the samples is conducted on the basis of the total amounts of protein included within the samples. To measure the neurite-outgrowth inhibition activity, part of the surface of a micropore filter or a culture container made of glass or plastics is coated with a test substance such as Semaphorin Y prepared as described above, and the activity is indicated, for example, by the inability of neurons cultured under conventional conditions to adhere to the coated area, or by a remarkable decrease in the rate of neurite outgrowth on the coated area, or by the inability of invasion of growing neurites from the outside of the coated area into the coated area because of its stopping on the border between the coated and non-coated areas or its avoidance from the coated area. When a cluster of cells expressing a test substance is co-cultured with neurons in a collagen gel, the inability of outgrowing neurite to enter the cluster of cells expressing the test substance may also be used as an indicator (A. Sophia et al., *Cell*, vol. 81, 621–629 (1995)).

Both neurons of CNS and PNS may be used as the cells for the above activity measurements. As described in the section "BACKGROUND ART", CNS in adult mammals naturally contains a large amount of regeneration (outgrowth) inhibitor. It is, therefore, extremely difficult to measure in vivo an inhibitory effect on neurite outgrowth of CNS-neuron, and such inhibitory effect is usually measured by an in vitro method as described above. Since these in vitro methods each have individual characteristics, it is preferred to use more than one method to confirm the activity. Although preferred neurons used for a measurement of the activity are CNS-neurons such as motor neurons in spinal cord or motor cortex, PNS-neurons in superior cervical ganglion and dorsal root ganglion may also be used because N135/250 known as a CNS-neuron regeneration inhibitor has proved to have effects such as neurite-growth inhibition and growth-cone collapse activities also on such PNS-neurons (*J. Cell Biol.*, 106, 1281–1288 (1988); *Science*, 259, 80–83 (1993)).

Specific examples of the modified proteins of this embodiment are described below.

Based on the structural comparison of known Semaphorins, most of the conserved amino acids are located in the semaphorin domain, suggesting that these conserved amino acids are essential for expression of the activity of Semaphorins. Furthermore, the present inventors have found that a modified Sema III protein in which aspartic acid residue at position 198 in its semaphorin domain has been substituted with glycine did not have the growth-cone collapse activity (see Reference example 1 below). Accordingly, the aspartic acid at position 198 of Sema III is believed essential for expression of the activity. The amino acid residues corresponding to this position are highly conserved in known Semaphorins, and they are all aspartic acid with a few exceptions in which glutamic acid is located at this position. It is, therefore, believed that the amino acid residue at this position is also essential for expression of the activity of Semaphorins other than Sema III. In Semaphorin Y of the present invention, the amino acid residue corresponding to the position 198 of Sema III is presumed to be aspartic acid at position 197 in the amino acid sequence shown in SEQ ID NO: 3, or aspartic acid at position 198 in the amino acid sequence of human Semaphorin Y shown in SEQ ID NO: 6.

Considering the above information, it is desirable to make the above-described deletions, substitutions and/or additions of amino acids at positions other than those conserved among Semaphorins, so as to retain the activity of Semaphorin Y in modified proteins. Particularly, it is desirable not to modify the aspartic acid at position 197 in rat Semaphorin Y shown in SEQ ID NO: 3 and the aspartic acid at position 198 in human Semaphorin Y. In order to substitute amino acids conserved among Semaphorins while retaining the activity of Semaphorin Y, it is desirable to substitute an amino acid having a similar side chain for the amino acid residue to be substituted. By substituting such amino acid having a similar side chain for a conserved amino acid, it may be possible to produce a modified protein which has an enhanced activity of Semaphorin Y. Such modified protein having the enhanced activity is highly suitable as a neurite-outgrowth inhibitor for PNS-neuron as will be described hereinafter in the section of the 22nd embodiment of the present invention.

In the above-noted embodiment, "a conserved amino acid" refers to an amino acid located at a position at which more than 50% of Semaphorin genes shown in FIG. 2 of *Cell*, 75, 1389–1399 (1993) or FIG. 1 of *Neuron*, 14, 941–948 (1995) share the same amino acid.

3) DNA Hybridizing Under Stringent Conditions to Semaphorin Y Gene

Of the above-mentioned DNAs, "a gene which hybridizes under stringent conditions to Semaphorin Y gene and which encodes a protein inhibiting neurite outgrowth" refers to a gene such as Semaphorin Y gene derived from a mammal, which hybridizes under stringent conditions to rat or human Semaphorin Y gene comprising the base sequence shown in SEQ ID NO: 1, 2, 4, or 5.

As used herein, "a gene which hybridizes under stringent conditions" refers to such a gene that hybridizes to rat or human Semaphorin Y gene, for example, when subjected to hybridization at a formamide concentration of about 45% (v/v) and a salt concentration of about 5× SSPE and at a temperature around 42° C., and washed at a salt concentration of about 2× SSPE and at a temperature around 42° C. Cloning of such genes may be achieved, for example, by screening cDNA or genomic libraries prepared from various animal tissues using all or part of DNA shown in SEQ ID NO: 1 or 4 as a probe. Such screening may be carried out by making reference to the standard texts such as "Molecular Cloning 2nd ed." (Cold Spring Harbor Laboratory Press (1989)).

Specific examples of the gene of this embodiment may include all the Semaphorin Y genes of mammal and avian. Between mammals or between mammal and avian, homologous genes have quite similar sequences, and usually more than 80%, in many cases more than 90%, of the base sequence are common to each other. All the mammal and avian Semaphorin Y genes, therefore, correspond to this embodiment. In other words, those genes which have a homology of 80% or above, and preferably of 90% or above, are included in this embodiment.

The 3rd embodiment of the present invention is a gene comprising DNA which hybridizes under stringent conditions to DNA comprising the base sequence shown in SEQ ID NO: 7, and which encodes a protein having a semaphorin domain.

In the above description, "DNA comprising the base sequence shown in SEQ ID NO: 7" refers to a fragment cloned by PCR using the sequence information of the DNA "R59527" which encodes, in part, a sequence consisting of seven amino acids well conserved among Semaphorins (Gln (or Arg)-Asp-Pro-Tyr-Cys-Ala (or Gly)-Trp (SEQ ID NO: 12)), and the DNA fragment corresponds to a region from position 1574 to position 1743 in the base sequence of rat Semaphorin Y shown in SEQ ID NO: 1, or a region from position 1524 to position 1693 in the base sequence of human Semaphorin Y shown in SEQ ID NO: 4.

The "stringent conditions" refers to those conditions described above in the section of the 2nd embodiment of the present invention.

Cloning of these DNAs is achieved by, for example, hybridization with DNA of SEQ ID NO: 7, and specifically may be carried out, for example, according to the procedures described in *TINS*, 15, 319–323 (1992) and references cited therein, and more specifically according to the following procedures.

That is, the cloning may be achieved by screening cDNA or enomic libraries prepared from various animal tissues using DNA consisting of the base sequence shown in SEQ ID NO: 7 as a probe. The screening may be carried out according to, for example, the procedures as described in Example 1. Preferred cDNA libraries are those derived from an adult tissue of CNS, and cDNA libraries derived from hippocampus, corpus striatum, and cerebellum are more preferred. As described above, the conditions shown in Example 1 or those described in *TINS*, 15, 319–323 (1992) and references cited therein may be used for the hybridization.

The DNA of this embodiment is also "DNA which encodes a protein having a semaphorin domain". As used herein, "semaphorin domain" refers to a domain consisting of 300–600 amino acid residues more than 20% of which are identical to those amino acids constituting the semaphorin domain of any one of ten known Semaphorins (G-Sema I, T-Sema, I, D-Sema II, H-Sema III, C-Collapsin, Sem A, Sem B, Sem C, Sem D, Sem E) described in, for example, *Cell*, 75, 1389–1399 (1993) or *Neuron*, 14, 941–948 (1995). Those proteins having a semaphorin domain more than 30% of which amino acids are identical to those amino acids in any one of the known Semaphorins are particularly preferred. The identity of amino acids is determined by comparison using, for example, DNASIS Ver. 2.0 (HITACH Software Engineering) under conditions of ktup=1 and cutoff=1. More preferred proteins are those in which ten or more cysteines, particularly twelve or more cysteines, of the thirteen cysteines conserved in semaphorin domains of the ten known Semaphorins (for example, those cysteines marked in FIG. 1 on page 942 of *Neuron*, 14, 941–948 (1995)) are conserved.

Examples of such gene of this embodiment may include Semaphorin genes which hybridize under stringent conditions to DNA comprising the base sequence shown in SEQ ID NO: 7 and which contain semaphorin domains and exhibit the neurite-outgrowth inhibition activity, including all of the Semaphorin Y genes of mammal and avian.

The 4th embodiment of the present invention is a protein obtained by expressing the gene of any one of the above items (1) to (3).

Typical examples of protein included in this embodiment are rat Semaphorin Y comprising the amino acid sequence shown in SEQ ID NO: 3, and human Semaphorin Y comprising the amino acid sequence shown in SEQ ID NO: 6. The rat or human Semaphorin Y contains a signal sequence at its N-terminus and such signal sequence is presumed to correspond to a region from position 1 to position 23 of the amino acid sequence shown in SEQ ID NO: 3 or from position 1 to position 24 of the amino acid sequence shown in SEQ ID NO: 6, respectively. Since the signal sequence is removed by processing during its transfer to membrane, such mature forms of Semaphorin Y are also included in this embodiment.

Preparation of the proteins of this embodiment may be achieved, for example, by ligating a cloned rat Semaphorin Y cDNA into a known expression vector such as pET or pCDM8, and introducing it into appropriate host cells to express and produce Semaphorin Y. The host cells may be prokaryotic or eukaryotic. For example, *Escherichia coli* strains or animal cell lines are already conventionally used for such purpose and are commercially or publicly available. Examples of animal host cells include COS-1, COS-7, CHO cells and the like.

To transform appropriate animal host cells with an expression plasmid, a known procedure such as DEAE-dextran method (*Current Protocols in Molecular Biology*, F. M. Ausubel et al. ed., John Wiley & Sons (1987)) may be used. As confirmed in Example 6, Semaphorin Y exists in the cell membrane faction which contains a sufficient amount of Semaphorin Y to be directly used in various assays. Therefore, various assays for activities of a protein of this embodiment may easily be conducted using a cell membrane fraction prepared from appropriate cells.

Furthermore, a protein of this embodiment may be purified by, for example, affinity purification using Semaphorin Y-recognizing antibodies described hereinafter in the section of the 16th embodiment of the present invention, or conventional column chromatography.

The 5th embodiment of the present invention is a gene encoding a protein which comprises an amino acid sequence wherein one or more amino acids are deleted, substituted and/or added in the rat or human Semaphorin Y shown in SEQ ID NO: 3 or 6 and which protein promotes neurite outgrowth. The 6th embodiment of the present invention is a protein obtained by expressing the gene of the 5th embodiment of the present invention.

In the genes of the above 5th embodiments, deletions, substitutions and/or additions may be introduced in the procedures similar to those used for a gene encoding a modified protein of the 1st embodiment of the present invention. Similarly, the pro motion effect on neurite outgrowth may easily be measured, for example, by adding Semaphorin Y in an assay system for Semaphorin Y activity described above in the section of the 1st embodiment of the present invention and further adding thereto a test substance (i.e., a candidate modified Semaphorin Y protein). For details, see the descriptions in the section of the 18th embodiment of the present invention.

Specific examples of the proteins of the 6th embodiment may be modified proteins of which neurite-outgrowth inhibition activity has been eliminated. Such modified protein lacking the neurite-outgrowth inhibition activity is expected to exert the promotion effect on neurite-outgrowth, when it binds to receptors for Semaphorin Y or to Semaphorin Y itself, by inhibiting the binding of Semaphorin Y to the receptors. As described above in the section of the 1st embodiment of the present invention, it has been suggested that the active site of Semaphorin may be located in the semaphorin domain, and particularly, it may be located at aspartic acid at position 197 in rat Semaphorin Y or aspartic acid at position 198 in human Semaphorin Y. Accordingly, in order to eliminate the semaphorin Y activity from the modified protein, it is desirable to introduce the deletions, substitutions and/or additions to the conserved amino acids in said semaphorin domain, preferably to the aspartic acid at position 197 in rat Semaphorin Y or to the aspartic acid at position 198 in human Semaphorin Y. In such cases, those substitutions in which an amino acid having a side chain of a distinct nature is substituted for the original amino acid are desirable. Also in the cases of Semaphorin Y other than that from human or rat, modifications are preferably made on aspartic acid at this position, that is, on amino acid residue at the position which corresponds to position 197 in rat Semaphorin Y or to position 198 in human Semaphorin Y when the amino acid sequence of said Semaphorin Y is aligned with that of rat or human Semaphorin Y so as to give the maximum identity.

Since the proteins of the 6th embodiment of the present invention promote neurite outgrowth as described above, some of these proteins will serve as CNS-neuron regeneration promoters as described hereinafter in the section of the 21st embodiment.

The 7th embodiment of the present invention is DNA which is cloned from a human cDNA library or a human genomic library, and which hybridizes under stringent conditions to DNA comprising at least part of rat or human Semaphorin Y DNA shown in SEQ ID NO: 1 or 4, respectively.

Methods of cloning are described in detail in, for example, "Molecular Cloning 2nd ed.", Cold Spring Harbor Laboratory Press (1989), and specifically include, for example, methods employing hybridization or PCR. Although a preferred library used herein is a genomic library derived from human, a cDNA library derived from CNS-neuron in the adult may also be used. Those methods employing hybridization may be carried out according to, for example, *TINS*, 15, 319–323 (1992) and references cited therein. Those methods employing PCR may be carried out according to, for example, "PCR" edited by McPherson et al., IRL Press (1991).

The DNAs thus cloned include not only the full length DNA but also its DNA fragments comprising more than 200 bases, or single-stranded forms (coding strands or complementary stands thereof) of said DNA fragments. Specific examples of DNA of the 7th embodiment of the present invention may include chromosomal DNAs containing 5' and/or 3' transcriptional control regions, noncoding sequences of exons, introns or the like, in addition to regions encoding amino acids. Such sequences which do not encode any amino acids are also quite useful, for example, in developing a medicine using antisense techniques described hereinafter.

The 8th embodiment of the present invention is an expression plasmid which expresses either the gene of the 1st, 2nd, 3rd or 5th embodiment, or DNA of the 7th embodiment of the present invention. The 9th embodiment of the present invention is a transformant transformed with the expression plasmid of the 8th embodiment. Furthermore, the 10th embodiment of the present invention is a process for producing a recombinant protein which process comprises culturing the transformant of the 9th embodiment and recovering the recombinant protein expressed. As described above in the section of the 4th embodiment of the present invention, methods of preparing an expression plasmid and a transformant, and methods of producing a recombinant protein, per se, are all well known to those skilled in the art.

The 11th embodiment of the present invention is a peptide comprising at least 6 amino acids of a protein of the 4th or 6th embodiment of the present invention. In this context, the limitation "at least 6 amino acids" is based on the fact that a minimal size of peptide capable of forming a stable structure consists of 6 amino acids, and preferred peptides are those consisting of 8 or more amino acids, more preferably of about 10–20 amino acids. A short peptide such as those consisting of about 10–20 amino acids can be synthesized on a peptide synthesizer, while a longer peptide can be obtained by preparing DNA through conventional genetic engineering, and expressing it in, for example, animal cells as described above. The peptide thus prepared can also be modified by conventional methods.

These peptides can be applied to pharmaceutical agents described hereinafter in the section of the 12th and 13th embodiments, and can also be used for producing antibodies.

The 12th embodiment of the present invention is a peptide of the 11th embodiment of the present invention which promotes neurite outgrowth. Such polypeptide may be prepared by the methods described above in the section of the 11th embodiment of the present invention. The promotion effect on neurite outgrowth can also easily be measured as described above in the section of the 5th embodiment of the present invention by adding Semaphorin Y to an activity assay system described above in the section of the 1st embodiment of the present invention and further adding thereto a test substance (i.e., a candidate peptide of Semaphorin Y). For details, see the descriptions in the section of the 18th embodiment of the present invention.

Specific examples of these peptides may be peptides which have lost the neurite-outgrowth inhibition activity of Semaphorin Y. A peptide lacking Semaphorin Y activity is expected to exert its neurite-outgrowth promotion effect, when it binds to receptors for Semaphorin Y or to Semaphorin Y itself, by inhibiting the binding of Semaphorin Y to the receptors. Some of such peptides will serve as CNS-neuron regeneration promoters as described hereinafter in the section of the 21st embodiment.

The 13th embodiment of the present invention is a peptide of the 11th embodiment of the present invention, characterized in that it contains the aspartic acid residue at position 198 of the amino acid sequence shown in SEQ ID NO: 6 or an amino acid residue corresponding to the position of said aspartic acid residue. Such peptides may be prepared by the methods described above in the section of the 11th embodiment.

As described above in the section of the 1st embodiment of the present inventions, the aspartic acid residue at position 198 of human Semaphorin Y shown in SEQ ID NO: 6 (in the case of rat, the aspartic acid residue at position 197) seems essential for expression of the activity of Semaphorin Y. Since this amino acid residue may possibly be involved in the binding between Semaphorin Y and its receptors, a peptide of this embodiment containing this amino acid residue may interfere the neurite-outgrowth inhibition activity of Semaphorin Y by binding to receptors for Semaphorin Y or to Semaphorin Y itself, resulting in promotion of neurite outgrowth. Some of the peptides having such effect will serve as CNS-neuron regeneration promoters as described hereinafter in the section of the 21st embodiment. Such neurite-outgrowth promotion activity can easily be measured as described above in the section of the 5th embodiment of the present invention by adding Semaphorin Y to an activity assay system described in the section of the 1st embodiment of the present invention, and further adding thereto a test substance (i.e., a candidate peptide of Semaphorin Y). For details, see the descriptions in the section of the 18th embodiment of the present invention.

In this embodiment, "an amino acid corresponding to the position of said aspartic acid" refers to an amino acid residue which is located at the position corresponding to position 198 in human Semaphorin Y, when the amino acid sequence of the protein of the 4th or 6th embodiment of the present invention is aligned with the amino acid sequence of human Semaphorin Y shown in SEQ ID NO: 6 so as to give the maximum identity. Accordingly, "a peptide characterized in that it contains an amino acid corresponding to the position of said aspartic acid" refers to a peptide which comprises such amino acid at the position corresponding to position 198 in human Semaphorin Y as well as flanking amino acids on either side thereof.

The 14th embodiment of the present invention is an antisense nucleotide, or chemically modified variant thereof, which is directed against a segment comprising at least eight or more bases in the gene of any one of the 1st to 3rd embodiments, or in DNA of the 7th embodiment of the present invention.

As used herein, "antisense nucleotide" refers to a so-called antisense oligonucleotide, antisense RNA, or antisense DNA, and it may be artificially prepared using a DNA synthesizer, or may be obtained by, for example, expressing a gene in the direction opposite to the usual case (i.e., in the antisense direction). For details, see the descriptions in the section of the 21st embodiment of the present invention.

These antisense nucleotides are used for inhibiting the expression of Semaphorin Y as described hereinafter in the section of the 15th embodiment of the present invention, and are also useful as laboratory reagents for, for instance, in situ hybridization. In the present invention, "a chemically modified variant" specifically refers to such a variant that is chemically modified so as to enhance the transferability of the antisense nucleotide into cells or the stability of the antisense nucleotide in the cells. Examples of such chemically modified variant are phosphorothioate, phosphorodithioate, alkylphosphotriester, alkyl phosphonate, alkyl phosphoamidate and the like derivatives ("Antisense RNA and DNA", WILEY-LISS, 1992, pp. 1–50, J. Med. Chem., 36, 1923–1937 (1993)). The chemically modified variant may be prepared according to, for example, the references cited just above.

The 15th embodiment of the present invention is an antisense nucleotide, or chemically modified variant thereof, of the 14th embodiment described above, characterized in that it inhibits the expression of the protein of the 4th embodiment of the present invention.

mRNAs produced by usual gene transcription are sense-strands, and the antisense nucleotides or chemically modified variants thereof can bind to such sense-strand mRNAs in cells to inhibit the expression of those particular genes. Therefore, the above-described antisense nucleotides or chemically modified variants thereof can inhibit the expression of Semaphorin Y, and can thereby inhibit the activity of Semaphorin Y. Some of antisense nucleotides or chemically modified variants thereof having such effect will serve as CNS-neuron regeneration promoters as described hereinafter in the section of the 21st embodiment of the present invention.

It can easily be determined whether a particular antisense nucleotide prepared, or a chemically modified variant thereof, has a desired inhibitory effect or not, by directly introducing the antisense oligonucleotide itself or by introducing a gene which produces said antisense RNA when transcribed, into cells expressing Semaphorin Y, and then determining whether the amount of the expressed Semaphorin Y is decreased or not.

Examples of antisense nucleotide having such inhibitory effect are those oligonucleotides having sequences complementary to either the coding region or the 5' noncoding region of Semaphorin gene of the above-described embodiments. Especially preferred are those antisense nucleotides having sequences complementary to the transcription initiation site, translation initiation site, 5' noncoding region, exon-intron junction region, or 5' CAP region.

The 16th embodiment of the present invention is an antibody against the protein of the 4th or 6th embodiment, or against the peptide of any one of the 11th to 13th embodiments. Such antibody can easily be produced by using mouse or rabbit according to the procedures described in, for example, "Current Protocols in Immunology", pp. 2.4.1–2.6.6 (1992, J. E. Coligan ed.). Monoclonal antibodies can also easily be produced by the methods described in the above-mentioned reference. Such antibodies may be used in affinity chromatography or screening of cDNA libraries, and as pharmaceutical or diagnostic agents, or laboratory reagents. Some of such antibodies have the activity of neutralizing Semaphorin Y. Such neutralizing activity can easily be determined, as described above in the section of the 5th embodiment of the present invention, by adding Semaphorin Y to an activity assay system described in the section of the 1st embodiment of the present invention, and further adding thereto a test substance (i.e., a candidate antibody against Semaphorin Y). Some of such neutralizing antibodies will serve as CNS-neuron regeneration promoters as described hereinafter in the section of the 21st embodiment of the present invention.

The 17th embodiment of the present invention is a pharmaceutical agent comprising, as an active ingredient, any one of all of the genes (DNAs), proteins, peptides, antisense nucleotides or chemically modified variants thereof, and antibodies of the present invention.

Among such pharmaceutical agents, CNS-neuron regenerators and neurite-outgrowth inhibitors for PNS-neuron will be described in the sections of the 21st and 22nd embodiments of the present invention, respectively. See, therefore, the sections of the 21st and 22nd embodiments for such applications.

It is being demonstrated in recent years that certain Semaphorins play important roles not only in the nervous system but also in non-nervous system. For example, it has been suggested that Semaphorin may probably act in inhibiting the growth of cardiac muscles (*Nature*, 383, 525–528 (1996)). Also in the immune system, certain Semaphorin has been suggested to be involved in aggregation and survival of B lymphocytes (*Proc. Nat. Acad. Sci. USA*, 93, 11780–11785 (1996)). It has also been suggested more recently that a certain Semaphorin may play some role in the immune reactions in rheumatism (*B.B.R.C.*, 234, 153–156 (1997)). Furthermore, involvement of Semaphorins in lung cancer has also been suggested (*Proc. Natl. Acad. Sci. USA*, 93, 4120–4125 (1996)).

Accordingly, Semaphorin Y of the present invention or its modified proteins, peptides, antisense nucleotides and the like are expected to be useful as antiallergic agents, immunosuppressive agents, or anti-tumor agents. For specific directions for use, dosage and the like, see the sections of the 21st and 22nd embodiments.

The 18th embodiment of the present invention is a method of screening for Semaphorin Y antagonists, characterized in that it employs the protein of the 4th embodiment of the present invention. As used herein, "Semaphorin Y antagonist" refers to a substance which inhibits, for example, the neurite-outgrowth inhibition activity of Semaphorin Y.

The screening is conducted by adding Semaphorin Y to an assay system for Semaphorin Y activity described in the section of the 1st embodiment of the present invention, and further adding thereto a test substance. In particular, inhibition of the Semaphorin Y activity resulted from the addition of the test substance to the culture medium throughout the incubation period or only temporarily in the incubation period can be used as an indicator in the Semaphorin Y activity assay conducted with added Semaphorin Y. It is also important to confirm that the test substance alone does not influence the survival and neurite-outgrowth of neurons at the same concentration. When both of these requirements are fulfilled, one can consider the test substance as a Semaphorin Y antagonist. Although it is preferred to prepare in advance the test substance in the form of aqueous solution, an organic solvent such as DMSO may also be used as a solvent. In any cases, it is important to minimize the volume of solvent so as to exclude any effects of the solvent on neurons. Specifically, the volume to be added should be less than an equal volume, preferably less than $\frac{1}{10}$ volume, and more preferably less than $\frac{1}{100}$ volume relative to the culture medium. Some of Semaphorin Y antagonists thus obtained will serve as CNS-neuron regeneration promoters as described hereinafter in the section of the 21st embodiment of the present invention.

The 19th embodiment of the present invention is Semaphorin Y antagonist obtained by the screening method of the 18th embodiment of the present invention. Such antagonist may have any structure and any form, provided that it inhibits the activity of Semaphorin Y.

The 20th embodiment of the present invention is Semaphorin Y antagonist of the 19th embodiment which comprises the protein of the 6th embodiment, the peptide of any one of the 11th to 13th embodiments, or the antibody of the 16th embodiment of the present invention. In other words, it is a protein of the 6th embodiment, a polypeptide of any one of the 11th to 13th embodiments, or an antibody of the 16th embodiment of the present invention which has an effect of inhibiting the activity of Semaphorin Y. Such antagonists can be identified by subjecting the above substances to the screening system of the 18th embodiment of the present invention, and some of the antagonists thus identified will serve as CNS-neuron regeneration promoters as described below in the section of the 21st embodiment of the present invention.

The 21st embodiment of the present invention is a CNS-neuron regeneration promoter, characterized in that it contains at least one of the antisense nucleotides or chemically modified variants thereof of the 14th or 15th embodiment, or Semaphorin Y antagonists of the 19th or 20th embodiment of the present invention. Since this embodiment relates to the use of substances in "regeneration therapy for CNS-neuron", specific directions for use, dose and the like, of the substances are described below.

1) Antisense Nucleotide or Chemically Modified Variant Thereof

Application of antisense nucleotides has been attempted in various diseases, and in recent years, it is also considered to be applicable in neurological disorders (*TINS* 20, No. 8, 321–322 (1997)).

As described above in the section of the 14th or 15th embodiment of the present invention, the antisense nucleotide or chemically modified variant thereof of the 14th or 15th embodiment of the present invention can be used for inhibiting expression of Semaphorin Y gene. Accordingly, such antisense nucleotide may decrease the abundance of the Semaphorin protein, and promote regeneration of CNS-neurons. Therapeutic methods using the nucleotide or the variant include those in which the antisense oligonucleotide or its chemically modified variant itself is administered, and those in which antisense RNA is produced in cells.

In the method in which the antisense oligonucleotide or its chemically modified variant is administered as such, a preferred antisense oligonucleotide has a length, for example, about 5–200 bases, more preferably 8–25 bases, and especially preferably 12–25 bases. Antisense oligonucleotide or its chemically modified variant may be formulated by mixing it with stabilizing agent, buffer, solvent and the like prior to its administration. Such formulation may be co-administered with, for example, an antibiotic, anti-inflammatory, or anesthetic agent. Although the formulation thus prepared may be administered via various routes, it is preferred to topically administered at a site in which neurons are notably disordered. Usually, regeneration of neuron takes several days to several months, and the formulation is administered every day or every several days to several weeks during the period. To avoid such frequent administrations, a sustained-release mini-pellet formulation may be prepared and embedded near the affected site. Alternatively, a formulation may be gradually and continuously administered to the affected site by means of, for example, an osmotic pump. The dose is typically adjusted so that the concentration at the site of action will be 0.1 nM to 10 μM.

In the method in which antisense RNA is produced in cells, a preferred antisense RNA has a length of, for example, more than 100 bases, preferably more than 300 bases, and more preferably 500 bases or more.

The methods by which a gene expressing an antisense RNA is introduced into a patient include an in vivo method in which the gene is directly introduced into cells in a living body, and an ex viva method in which the gene is introduced into particular cells ex vivo and the cells are returned into the body (Nikkei Science, April, 1994, pp. 20–45; Gekkan-Yakuji, 36 (1), 23–48 (1994); Jikkenn-Igaku-Zokan, 12 (15), 1994; and references cited therein). An in vivo method is more preferred.

Such in vivo methods include a method employing recombinant viruses and other methods (Nikkei Science, April, 1994, pp. 20–45; Gekkan-Yakuji, 36 (1), 23–48 (1994); Jikken-Igaku-Zokan, 12 (15), in its entirety (1994); and references cited therein).

The methods employing recombinant viruses may include the methods in which Semaphorin gene is incorporated into a virus genome of, for example, retrovirus, adenovirus, adeno-associated virus, herpesvirus, vaccinia virus, poliovirus, or sindbis virus, and the recombinant virus is introduced into a living body. Among these methods, those employing retrovirus, adenovirus or adeno-associated virus are particularly preferred.

Other methods may include a liposome method or a lipofectin method. The liposome method is particularly preferred.

For the ex vivo methods, a micro-injection method, the calcium phosphate method, electroporation and the like may also be used, besides those techniques described above.

Administration of the gene to a patient is carried out via appropriate routes depending on particular disease or symptom to be treated, and the like. For example, it may be administered intravenously, intraarterially, subcutaneously, or intramuscularly, or directly administered into an affected site such as neuron. For example, when spinal cord is infected with the recombinant viruses, the expression of Semaphorin gene is inhibited exclusively in the spinal cord. Expression of antisense oligonucleotide of the present invention typically lasts several days to several months, and such single infection is sufficient to allow regeneration of neuron. The gene may also be re-infected, when weakly expressed. When administered by an in vivo method, the gene may be formulated in the form of, for example, a solution, and typically it is formulated in the form of an injection containing Semaphorin gene as an active ingredient to which conventional carrier and the like may be added, if necessary. In the case of liposomes or membrane-fused liposomes (such as Sendai virus (HVJ)-liposomes) containing Semaphorin gene, the liposome preparations may be in the form of a suspension, a frozen preparation, a centrifugally-concentrated frozen preparation or the like.

Although the amount of Semaphorin gene in the formulation may vary depending on the disease to be treated, the age and weight of the patient, and the like, it is typically 0.0001–100 mg, and preferably 0.001–10 mg, and such formulation is preferably administered once every several days to several months.

2) Modified Protein of Semaphorin Y

As described above in the sections of the 5th and 6th embodiments of the present invention, one can prepare a modified Semaphorin Y of which neurite-outgrowth inhibition activity on CNS-neuron has been eliminated. When administered into a living body, such modified protein is expected to bind to receptors for Semaphorin Y in place of Semaphorin Y, resulting in inhibition of Semaphorin Y activity and promotion of regeneration of CNS-neuron.

Such modified protein of Semaphorin Y is formulated with stabilizer, buffer, and diluent, and administered to a patient for therapy. Such formulation may be administered via various routes, and it is preferred to topically administer to the focal site. Since regeneration of neuron typically takes several days to several months, the formulation is administered once or more in order to continuously inhibit Semaphorin Y activity throughout the period. When administered more than once, it is desirable to administer it every day or repeatedly at appropriate intervals. When administered to CNS by injection, for example, into spinal cord, several hundreds μg to 2 g, preferably less than several tens mg, are used per administration. To reduce the administration frequency, it may be administered using a sustained-release formulation or gradually administered over a long period by means of, for example, an osmotic pump. Alternatively, it may be administered by grafting cells expressing such modified Semaphorin Y protein into a living body.

3) Peptide of Semaphorin Y

Some of the peptides of any one of the embodiments from 11th to 13th of the present invention suppress the neurite outgrowth inhibition activity of Semaphorin Y on CNS-neuron by inhibiting the binding of Semaphorin Y to its receptors, resulting in promotion of CNS-neuron regeneration. Examples of peptide having such effect include a peptide characterized in that it contains aspartic acid residue at position 198 of human Semaphorin Y shown in SEQ ID NO: 6 or an amino acid residue at the position corresponding to that of said aspartic acid residue, as described above in the section of the 13th embodiment of the present invention. The suppression may be any one of competitive, noncompetitive, uncompetitive, and allosteric inhibitions.

As for the methods of formulating or administering such polypeptides, and their doses, see the above section "2) Modified protein of Semaphorin Y".

4) Antibody Against Semaphorin Y

A neutralizing antibody which neutralizes the activity of Semaphorin Y is expected to promote the regeneration therapy of CNS-neuron by inhibiting Semaphorin Y activity, when administered into a living body.

The methods of formulating or administering such neutralizing antibodies and their doses may be the same as described in the above section "2) Modified protein of Semaphorin Y". Alternatively, a method in which cells producing a monoclonal antibody are grafted directly into CNS may also be used, as described in *Nature*, 343, 269–272 (1990).

The 22nd embodiment of the present invention is a neurite outgrowth inhibitor for PNS-neuron, characterized in that it contains at least one of the proteins of the 4th embodiment of the present invention. Although the proteins of the 4th embodiment of the present invention may inhibit the neurite outgrowth of CNS-neuron, they are also expected to inhibit the neurite outgrowth of PNS-neuron, since PNS-neuron also probably expresses receptors for Semaphorin Y, and receptors for other Semaphorins also probably react with Semaphorin Y. Accordingly, they may serve as therapeutic agents for atopic dermatitis, pain or other diseases by virtue of their inhibition activity on neurite outgrowth of PNS-neuron.

As for the methods of formulating or administering such proteins, and their doses, see the above section "2) Modified protein of Semaphorin Y".

The 23rd embodiment of the present invention is a transgenic animal in which either the gene of any one of the 1st to 3rd and 5th embodiments, or DNA of the 7th embodiment of the present invention has been artificially inserted into its chromosome, or has been knocked out.

As apparent from the following references, one skilled in the art can quite easily produce a transgenic animal which expresses the gene of the 1st, 4th, 7th, or 9th embodiment of the present invention, in the light of the gene information on Semaphorin Y of the present invention: "Manipulation of Mouse Embryo" edited by B. Hogan et al., 1986, Cold Spring Harbor Laboratory; Shinichi Aizawa, "Gene Targeting", 1995, Yodosha, etc. Accordingly, the transgenic animal thus produced is naturally included within the scope of the present invention. The transgenic animal thus produced is very useful as an animal model for developing pharmaceuticals or as an animal used for screening of pharmaceuticals. Furthermore, a so-called knockout animal in which the gene of the 1st, 4th, 7th, or 9th embodiment of the present invention has been deleted is characterized in that it does not contain such gene. As described in literatures, or as apparent from the common knowledge in the art, such knockout animals cannot be produced without the gene information on Semaphorin Y of the present invention. It goes without saying, therefore, that such knockout animals are included within the scope of the present invention.

While Semaphorin Y has an important in vivo function relating to regeneration of neurons as described above, it has been also suggested as mentioned above that Semaphorin Y may have other unknown functions such as immunosuppression (*Cell*, 75, 1389–1399 (1993)). Accordingly, it is quite important to investigate the expression of Semaphorin Y gene or the distribution and function of Semaphorin Y protein for studying this technical field or for diagnosing patients with neurological disorders or other diseases. The present invention can also provide gene probes, antibodies, recombinant proteins, transgenic animals and the like which can be used for such purposes.

Total RNAs were extracted from various tissues of six-weeks old rats, electrophoresed on 1% agarose-formamide gel, blotted onto a filter, and hybridized with a $^{32}$P-labeled rat Semaphorin Y DNA probe to determine the distribution of Semaphorin Y mRNA expression. Fifteen μg of RNA was loaded in each lane. The upper panel shows the result of autoradiography. The positions corresponding to 18S and 28S ribosomal RNAs are indicated at the left margin of the panel. The lower panel shows the ethidium bromide staining of the gel. The upper and lower bands correspond 28 and 18S ribosomal RNAs, respectively.

Figure 2:
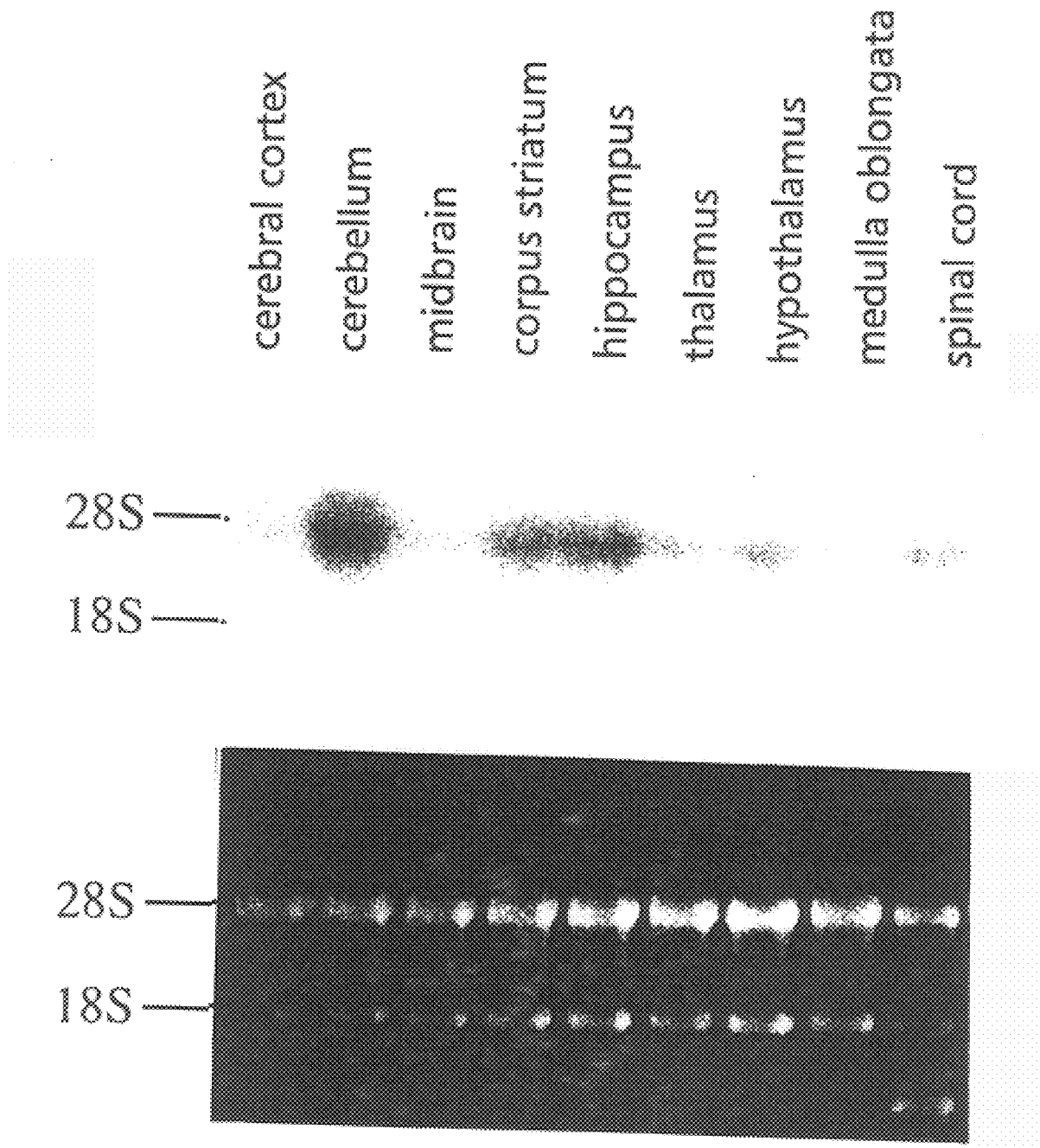

FIG. 2 shows a picture of electrophoresis indicating distribution of Semaphorin Y expression among CNS tissues determined by Northern analysis.

Total RNAs were extracted from CNS tissues of six-weeks old rats, electrophoresed on 1% agarose-formamide gel, blotted onto a filter, and hybridized with a $^{32}$P-labeled rat Semaphorin Y DNA probe to determine the distribution of Semaphorin Y mRNA expression. Fifteen μg of RNA was loaded in each lane. The upper panel shows the result of autoradiography. The positions corresponding to 18S and 28S ribosomal RNAs are indicated at the left margin of the panel. The lower panel shows the ethidium bromide staining of the gel. The upper and lower bands correspond 28 and 18S ribosomal RNAs, respectively.

Figure 3:
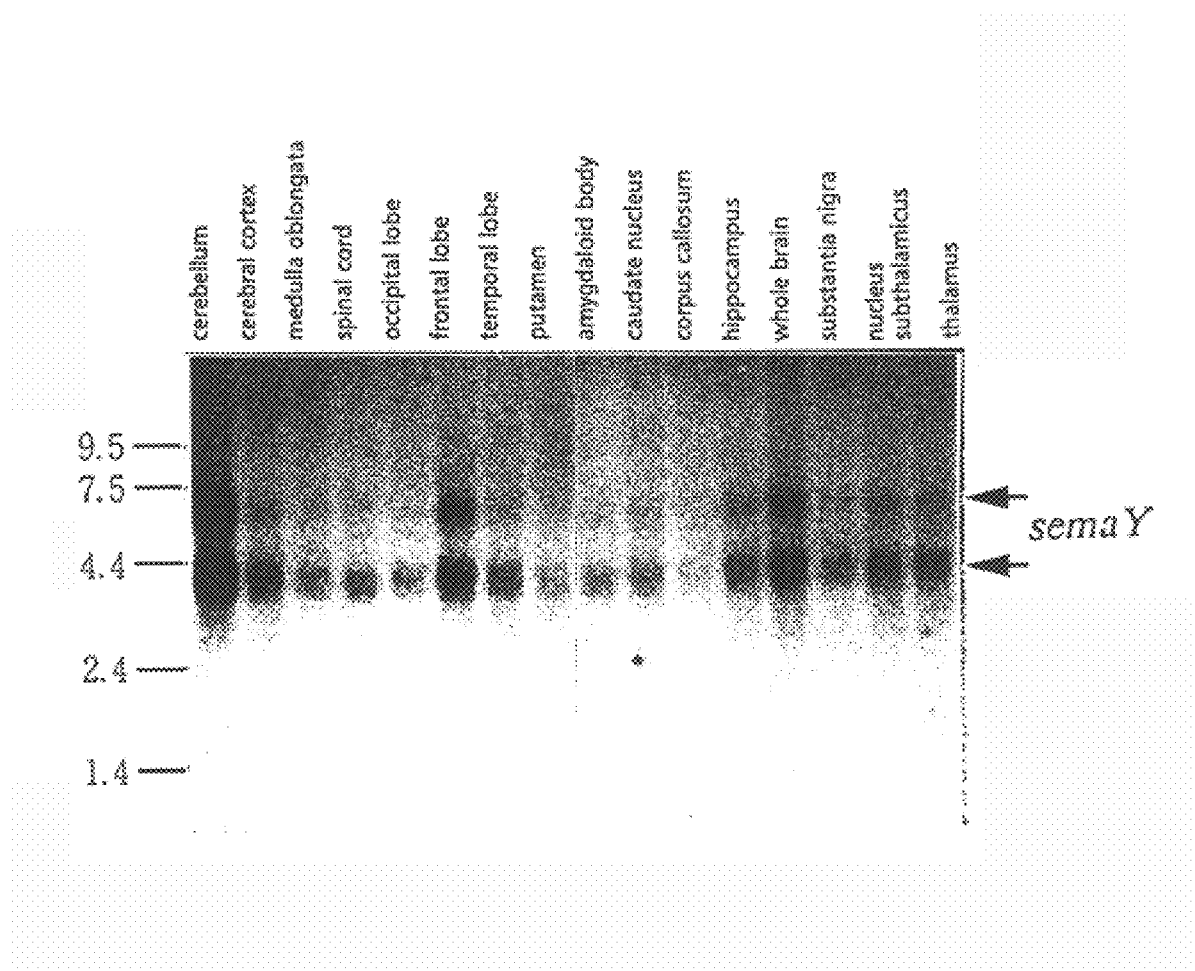

FIG. 3 shows a picture of electrophoresis indicating distribution of Semaphorin Y mRNA expression among human CNS tissues determined by Northern analysis.

A Membrane filter onto which mRNAs prepared from various regions of human CNS tissues have been transferred after being electrophoresed (2 μg/lane) (Clontech) was hybridized with $^{32}$P-labeled Semaphorin Y DNA probe to determine the distribution of Semaphorin Y mRNA expression. The figure shows the result of autoradiography. In this figure, the arrows indicate the positions of Semaphorin Y mRNA bands. Positions of size makers are indicated in kb at the left margin of the figure.

Figure 4:
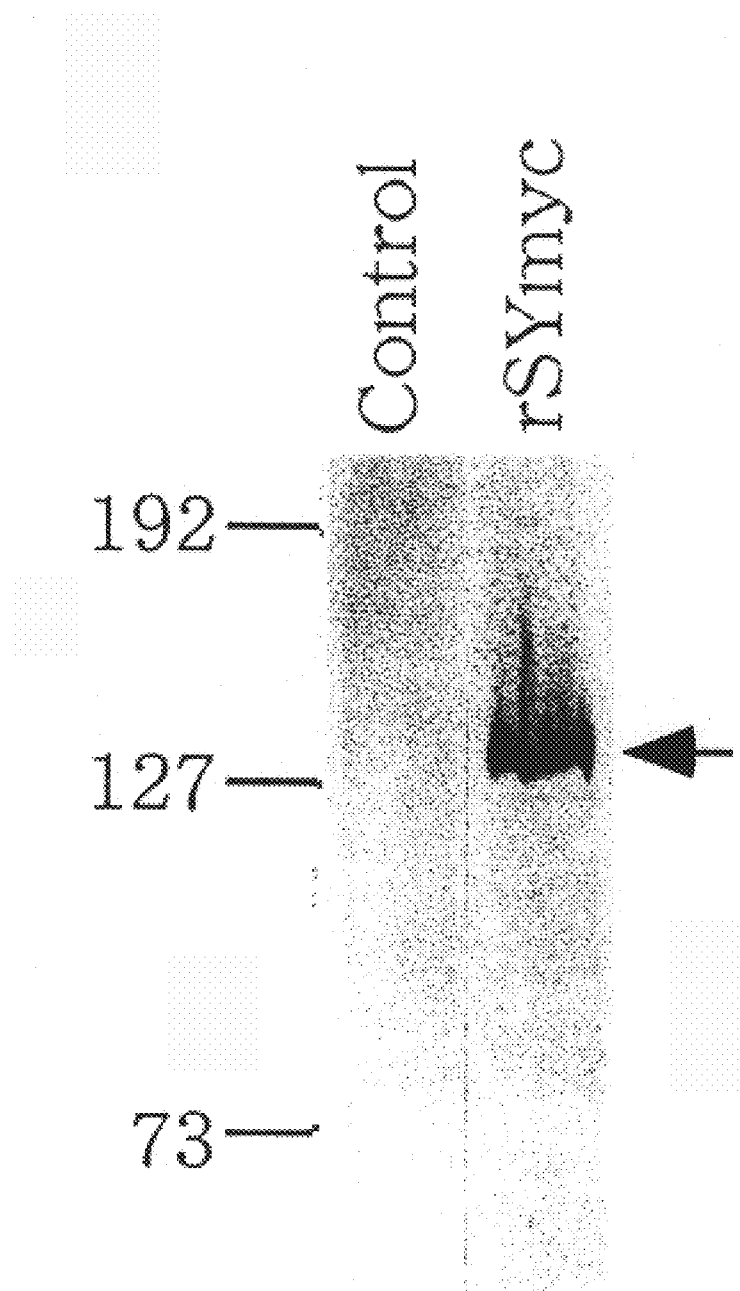

FIG. 4 shows a picture of electrophoresis indicating expression of Semaphorin Y protein in COS 7 cells.

An expression plasmid for Semaphorin Y having additional 10 amino acids derived from human c-Myc added at its C-terminus was constructed, and introduced into COS 7 cells for transient expression (indicated as rSYmyc). A plasmid containing no Semaphorin Y gene was used as control (indicated as Control). At day 3 after introducing plasmids, the cells were harvested, and the membrane fraction was prepared. The membrane fraction was fractionated by SDS-PAGE, and then subjected to Western blotting using an anti-Myc antibody. In this figure, the arrow indicates the position of the band of Semaphorin Y protein having added Myc peptide. Positions and molecular weights of size makers are indicated in kD at the left margin of the figure.

Figure 5:
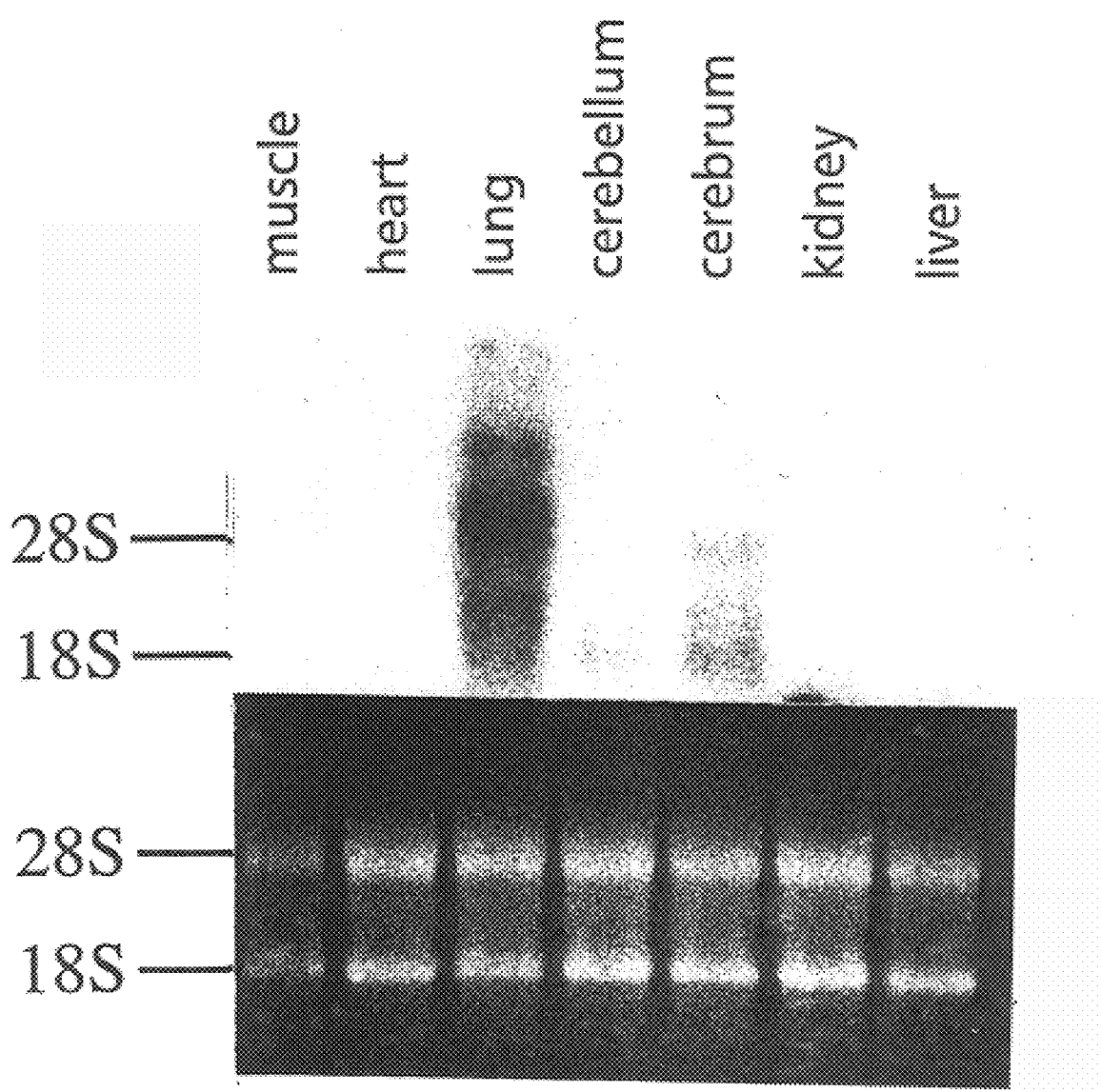

FIG. 5 shows a picture of electrophoresis indicating the in vivo distribution of Semaphorin III expression among various tissues determined by Northern analysis.

Total RNAs were extracted from various tissues of adult rats, electrophoresed on 1% agarose-formamide gel, blotted onto a filter, and hybridized with $^{32}$P-labeled mouse Semaphorin III DNA probe to determine the distribution of Semaphorin III mRNA expression. Fifteen μg of RNA was loaded in each lane. The upper panel shows the result of autoradiography. The positions of 18S and 28S ribosomal RNAs are indicated at the left margin of the figure. The lower panel indicates the ethidium bromide staining of the gel. The upper and lower bands correspond to 28S and 18S ribosomal RNAs, respectivly.

EXAMPLES

Fundamental procedures for experiments are described in detail in many publications such as "Molecular Cloning, 2nd Ed." edited by Maniatis et al. (Cold Spring Harbor Laboratory Press, 1989), "Current Protocols in Molecular Biology" edited by Ausubel et al. (John Wiley & Sons, 1987), and "Saibo-Kogaku-Jikken Protocols" edited by Department of Oncology, The Institute of Medical Science, The University of Tokyo (Shujunsha, 1991). The present invention is not intended to be limited by the following examples, and the examples may be of course modified as usual.

Example 1

Isolation of Rat Semaphorin Y Gene (1) Search Through Database for a Novel Semaphorin Gene Using the dbEST database of the National Center for Biotechnology Research (Bethesda, Md., US), search was performed for a sequence which encodes an amino acid sequence relatively well conserved in known Semaphorin genes and which is found in only cDNAs from postnatal brain but not in cDNAs from peripheral tissues. As a result, the base sequence of File No. R59527 proved to encode a sequence consisting of seven amino acids common to known Semaphorin genes (Gln (or Arg)-Asp-Pro-Tyr-Cys-Ala (or Gly)-Trp (SEQ ID NO: 12)). However, the sequence information of R59527 consisting of 238 bases is so short compared with the cDNAs for known Semaphorin genes, and only several percent of the total bases could be translated to a sequence common to those in known Semaphorins. In addition, the reading frame could not be determined because the sequence of R59527 is not the one finally determined. It was, therefore, impossible to conclude that the base sequence of R59527 is part of a novel Semaphorin gene. Then, the inventors firstly confirmed that a gene containing the above sequence is expressed in the adult brain, and then sought to clone the full length cDNA containing the above sequence and determine its gene structure.

(2) Confirmation of the Expression of the Gene Containing the Sequence of R59527 in the Brain To confirm that the gene is expressed in the adult human CNS, two DNA primers bounding a segment of about 170 bp, 5' TGGCTGTATTGTCTACCT 3' (SEQ ID NO: 8) and 5' TGGATTCCTGGTTCCNAGCC 3' (SEQ ID NO: 9), were synthesized on the basis of the base sequence of R56527, and used in PCR under conventional conditions together with cDNAs prepared from a human brain cDNA library (Clontech) as templates. As a result, about 170 bp fragment was amplified as expected. The DNA was then cloned into pCRII (Invitrogen) according to the manufacturer's protocol, and the base sequence was determined to confirm that the fragment has the same base sequence as that of R59527. More than 98% of the sequence thus obtained (SEQ ID NO: 7) coincided with that of R59527, confirming that a gene containing the sequence of R59527 is expressed in the adult human brain.

(3) Isolation of Rat Semaphorin Y Gene

Using the 170 bp fragment cloned in (2), which corresponds to part of R59527, as a probe, the inventors cloned a full-length CDNA containing the sequence of the probe and determined the structure. Since preparation of rat cDNA library is easier than that of human cDNA library, the rat gene was firstly cloned. A cDNA library was prepared by conventional methods described in the above-mentioned laboratory manuals, using mRNAs prepared from rat brain and muscle by conventional procedures with Lambda Zap II (λZapII) cDNA Library Preparation Kit (Stratagene). About 150 thousand plaques were then generated on agar plates using the CDNA library, and the plaques were transferred onto nylon membranes (Nippon Pall). After denaturing and neutralizing the DNAs, they were fixed with ultraviolet rays of 0.6 J/cm$^2$, and used in hybridization. The hybridization was conducted by placing the nylon membrane and the 170 bp DNA fragment labeled with $^{32}$P (prepared using Megaprime DNA Labeling System (Amersham)) as a probe in a hybridization buffer (45% (v/v) formamide, 5× SSPE (1× SSPE consists of 0.15 M sodium chloride, 10 mM sodium dihydrogenphosphate, and 1 mM ethylenediaminetetraaceticacid disodium salt, adjusted to pH 7.0), 2× Denhardt's solution (Wako Pure Chemical. Industries), 0.5% (w/v) sodium dodecyl sulfate (SDS), 20 µg/ml salmon sperm DNA (Wako Pure Chemical Industries)) and allowing them to stand at 42° C. for 48 hours: After the reaction, the nylon membrane was washed 2–3 times in 2× SSPE, 0.5% (w/v) SDS at room temperature for 10 min, and then 2–3 times in 2× SSPE, 0.5% (w/v) SDS at 42° C. for 10 min. The filters thus prepared were analyzed using BAS 2000 Bio-Imaging Analyzer (Fuji Film), and 6 positive signals were obtained. Plaques corresponding to the positive signals were excised from the agar plates, placed in 500 µl of SM buffer (100 mM sodium chloride, 15 mM magnesium sulfate, 50 mM Tris (pH 7.5), 0.01% gelatin) supplemented with 20 µl of chloroform, and left stand overnight at 4° C. to elute the phages. The recombinant lambda phages thus obtained were subjected to a secondary screening according to the procedures as described above, and single plaques were isolated. The phages thus obtained were treated in the following manner for in vivo excision of a phagemid containing the cDNA insert, according to the protocols supplied by Stratagene. Agar gels containing the 4 single plaques obtained in the secondary screening were each placed in 500 µl of SM buffer, supplemented with 20 µl of chloroform, and then allowed to stand overnight at 4° C. Two hundred fifty µl of the phage solution obtained, 200 µl of E. coli XL-1 Blue MRF' suspended in 10 mM magnesium chloride at $OD_{600}$= 1.0, and 1 µl of ExAssist helper phage (>1×10$^6$ pfu/ml) were mixed, and incubated at 37° C. for 15 min. Then, 3 ml of LB medium (prepared by mixing 0.5% (w/v) sodium chloride, 1% (w/v) Bactotrypton (Difco), and 0.5% (w/v) yeast extract (Difco) and the mixture was adjusting to pH 7.0 using 5 M sodium hydroxide) was added, and the mixture was shaken at 37° C. for 2–3 hours. The cells were removed by centrifuging at 2000×g for 15 min, and the supernatant was heat-treated at 70° C. for 15 min. The supernatant was then centrifuged again at 2000×g for 15 min, and recovered as a stock solution of a phagemid containing the cDNA insert. An aliquot (10–100 µl) of the phagemid stock solution was mixed with 200 µl of E. coli SOLR ($OD_{600}$=1.0), incubated at 37° C. for 15 min. Then, 10–50 µl of the mixture was plated onto an ampicillin plate, and incubated overnight at 37° C. to obtain E. coli strain which contained the phagemid corresponding to the above positive plaque.

(4) DNA Sequencing

The base sequence of the cDNA clone thus obtained was analyzed on Perkin-Elmer Model 377 DNA Sequencer to determine the complete base sequence. The reaction was carried out using PRISM Dye termination kit (Perkin-Elmer). The DNA base sequence thus determined (3195 bases), the putative open reading frame (2787 bases), and the amino acid sequence (929 amino acids) are shown in SEQ ID NOs: 1, 2, and 3, respectively.

The protein contained a so-called semaphorin domain at positions 46 through 570 in the amino acid sequence, definitely confirming that the protein belongs to the Semaphorin family. The protein encoded by the gene was thus designated Semaphorin Y. In addition, since the base sequence of positions 1574 through 1811 in the Semaphorin Y gene shown in SEQ ID NO: 1 had 89% identity with the whole sequence of R59527 consisting of 238 bp, it was confirmed that R59527 is a partial sequence of human Semaphorin Y gene.

Example 2

Distribution of Rat Semaphorin Y Expression Determined by Northern Analysis

In order to determine the distribution of Semaphorin Y gene expression among rat tissues, RNAs were prepared from various tissues and used in Northern analysis. RNAs were prepared as follows using various rat tissues according to AGPC method (Takashi Tuji and Toshikazu Nakamura, *Jikken-Igaku*, vol. 9, 1991, pp. 1937–1940; M. F. Ausubel et al. ed., "Current Protocols in Molecular Biology", 1989, pp. 4.2.4–4.2.8, Greene Pub. Associates & Wiley-Interscience). Briefly, 10 ml of a denaturing solution (4M guanidine thiocyanate, 25 mM sodium citrate (pH 7.0), 0.5% sarkosyl, 0.1 M 2-mercaptoethanol) was added to each 1 g of excised tissues, and quickly homogenized using a Polytron homogenizer. To the homogenate, 0.1 volume of 2 M sodium acetate (pH 4.0), 1 volume of water-saturated phenol, and 0.2 volumes of chloroform-isoamyl alcohol (49:1) were added, and the mixture was vigorously stirred. After centrifugation, the aqueous layer was isolated, an equal volume of isopropyl alcohol was added thereto, and the mixture was allowed to stand at −20° C. for 1 hour. The precipitate was recovered by centrifugation, and dissolved again in 2–3 ml of the denaturing solution per 1 g tissue. An equal volume of isopropyl alcohol was added, and the mixture was allowed to stand at −20° C. for 1 hour, and then RNA was centrifuged. The precipitate was washed with 75% ethyl alcohol, dried briefly, and then dissolved in an appropriate amount of water.

Figure 1:
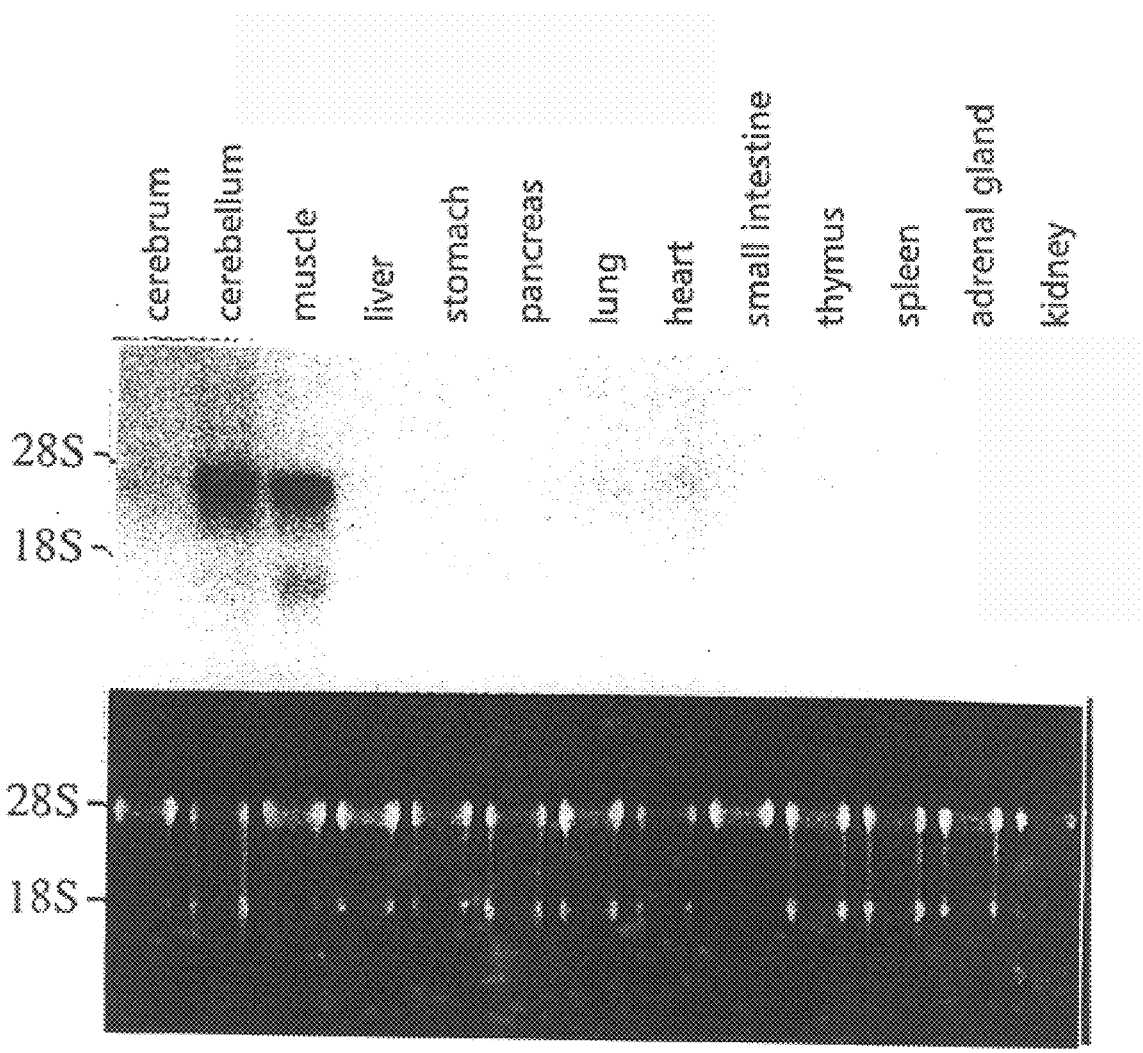
FIG. 1 shows a picture of electrophoresis indicating distribution of Semaphorin Y expression among various tissues determined by Northern analysis.

Subsequently, electrophoresis and Northern blotting of RNAs were performed by conventional methods described below. RNAs prepared from various tissues were firstly electrophoresed on 1% agarose gel containing formaldehyde. The gel was shaken in 50 mM NaOH for 20 min, and then in 10× SSPE for 40 min. The RNAs were then blotted onto a nylon membrane (Biodyne B, Nippon Pall) by means of capillary transfer, and fixed using a UV cross-linker (Stratagene) (0.6J/cm$^2$) for use in hybridization. A probe was prepared as follows. Firstly, PCR was carried out using two primers, 5' TGTGTAAACGTGACATGG 3' (SEQ ID NO: 10) and 5' TGCTAGTCAGAGTGAGGA 3' (SEQ ID NO: 11), with rat Semaphorin Y cDNA obtained in Example 1 as template to amplify a fragment of 477 bp. This fragment was cloned into pCR II in the same manner as described above, and the base sequence was determined to confirm that it was a fragment of rat Semaphorin Y gene. Using this plasmid DNA as template, PCR was carried out in conventional manner with the above primers to amplify the aimed fragment of 545 bp. The amplified DNA separated and purified using agarose gel was labeled with $^{32}$P using Megaprime DNA Labeling System (Amersham) as described in Example 1, and used as a probe. Hybridization was carried out by placing the nylon membrane and the probe DNA in the same hybridization buffer as described above in (2) and allowing them to stand at 42° C. for 48 hours. After the reaction, the nylon membrane was washed 2–3 times in 2× SSPE, 0.5% (w/v) SDS for 10 min at 42° C., and then 2–3 times in 2× SSPE, 0.5% SDS (w/v) at 55° C. for 10 min. Radioactivity on the membrane was then analyzed using BAS 2000 Bio-Imaging Analyzer. As shown in FIGS. 1 and 2, the result demonstrated that mRNA for Semaphorin Y was widely expressed in the adult CNS, whereas the expression was not detected in peripheral tissues with the only exception of muscle, exhibiting the characteristic features expected with Semaphorin gene as CNS-neuron regeneration inhibitor.

Example 3

Sequence Determination of Human Semaphorin Y

Since R59527 has proved to be part of human Semaphorin Y gene as described above, an EST clone containing the sequence of R59527 (#41581) was obtained from Genome Systems Inc. (US), and the complete base sequence was determined by the method described above. The determined base sequence had a high homology to the entire base sequence for rat Semaphorin Y shown in SEQ ID NO: 1 with 74% of the bases being the same. In addition, the 5' region of the base sequence contains a stretch, presumably part of the open reading frame, which could be continuously translated into 427 amino acids. This amino acid sequence had an identity of 82% with that of the region from position 504 to position 929 of rat Semaphorin Y gene shown in SEQ ID NO: 3, indicating that the sequence was certainly part of human Semaphorin Y. However, the sequence corresponding to the N-terminal of human Semaphorin Y could not be determined from this clone #41581. In order to determine the base sequence for human Semaphorin Y in full length, human hippocampus and forebrain cDNA libraries purchased from Stratagene were screened as described above using various rat Semaphorin Y cDNA fragments as probes to obtain a clone #10. The base sequence of the clone #10 determined by the same procedures as described above overlapped with the above clone #41581 by about 200 bases, and further contained in its 5' region a cDNA sequence consisting of more than 1700 bases. The complete base sequence (3432 bases) constructed from #41581 and #10, the open reading frame (2790 bases), and the amino acid sequence (930 amino acids) for human Semaphorin Y are shown in SEQ ID NOs: 4, 5, and 6, respectively. Human Semaphorin Y was 87% identical at the amino acid level to rat Semaphorin Y.

*E. coli* strain SOLR (hSY10), a transformant obtained by introducing the plasmid hSY10, which incorporates the insert of the above clone #10 (the region corresponding to cDNA for human Semaphorin Y) in a vector pBluescript, into *E. coli* strain SOLR, has been deposited at The National Institute of Bioscience and Human Technology (1-1-3 Higashi, Tsukuba, Ibaraki, Japan) under Deposit No. FERM BP-6021 on Jul. 11, 1997.

*E. coli* strain DH10B (N041581), a transformant obtained by introducing the plasmid N041581, which incorporates the insert of the above clone #41581 (the region corresponding to cDNA for human Semaphorin Y) in a vector Lafmid BA, into *E. coli* strain DH10B, has been deposited at The National Institute of Bioscience and Human Technology (1-1-3 Higashi, Tsukuba, Ibaraki, Japan) under Deposit No. FERM BP-6022 on Jul. 11, 1997.

Example 4

Distribution of Human Semaphorin Y Expression Determined by Northern analysis

Northern analysis was performed as described in Example 2 with human mRNA blotting membrane (Clontech) using a rat Semaphorin Y cDNA fragment consisting of 479 bp from position 832 to position 1310 in SEQ ID NO: 1 obtained by PCR as a probe to determine the distribution of Semaphorin Y mRNA expression among various regions in human adult CNS tissues. As shown in FIG. 3, human Semaphorin Y mRNA was widely expressed in various regions of the adult CNS tissues, and a particularly high expression was observed in the cerebellum.

As stated above, Semaphorin Y is widely expressed in human CNS tissues as is the case with its rat homologue, indicating that Semaphorin Y may be responsible for functions common to rodents and primates.

Example 5

Expression of Semaphorin Y in Animal Cells

A fragment encoding Myc tag (SEQ ID NO:13) having the sequence Asp-Ile-Gly-Gly-Glu-Gln-Lys-Lue-Ile-Ser-Glu-Glu-Asp-Leu was inserted just before the stop codon of rat Semaphorin Y gene, and the recombinant gene was introduced into an expression plasmid pUCSRα. The expression plasmid was transfected into COS 7 cells according to DEAE-dextran method ("Current Protocols in Molecular Biology" edited by F. M. Ausubel, John Wiley & Sons, 1987), and the cells were harvested with a cell scraper after 48 hours. Harvested cells were homogenized in the presence of Solution A containing protease inhibitors (Hank's physiological saline containing 10 mM HEPES pH 7.4, 1 mM EDTA, 50μM leupeptin, 2 μM pepstatin, 0.5 mM PMSF, and 7.8 mTIU/ml aprotinin) and the homogenate was separated into precipitate and supernatant by high-speed centrifugation at 12,000 g for 10 min. The precipitate from the high-speed centrifugation which contained the membrane fraction was washed twice with Solution A, suspended in 2 volumes of 2.25 M sucrose/PBS, and overlaid onto 2.25 M sucrose/PBS. After 0.8 M sucrose/PBS was further overlaid onto the top, it was centrifuged at 12,000 g for 20 min. The membrane fraction was recovered from the lower interface, further washed twice, and stored at −80° C. until use.

The membrane fraction obtained was subjected to SDS-PAGE (10%–20% gradient gel), and then to Western blotting in conventional manner to confirm the production of Semaphorin Y of the present invention. During this procedure, an anti-Myc antibody 9E10 (Calbiochem) and an alkaline phosphatase-labeled anti-mouse IgG antibody (Biosource) were used as the primary and secondary antibodies, respectively. The result of Western blotting showed a specific band at the position corresponding to about 130 kDa as shown in FIG. 4, confirming that Myc-tagged rat Semaphorin Y protein was expressed in COS cells and existed in the membrane.

Example 6

Activity Measurement of Semaphorin Y

The membrane fraction obtained in Example 5 and another membrane fraction prepared in the same manner from COS 7 cells untransfected with Semaphorin Y are each added to culture medium for neurons such as CNS-neurons or dorsal root ganglion cells, and the growth-corn collapse activities are compared by the method described in M. Igarashi et. al., Science, 259, 77–79 (1993). The result demonstrates that the membrane fraction from COS 7 cells transfected with the expression plasmid for Semaphorin Y has a significantly high growth-corn collapse activity.

Reference Example 1

Identification of the Site Essential to the Semaphorin Activity Using Semaphorin III PCR was conducted on the basis of the sequence information on Semaphorin III described in *Neuron,* 14, 941–948 (1995), and the structural gene of Semaphorin III was incorporated into an expression plasmid pUCSRα. The expression plasmid was then introduced into COS 7 cells by DEAE-dextran method. After 2 days, the Semaphorin III activity contained in the culture supernatant was determined by a method similar to that described in *Cell,* 75, 217–227 (1993), using the growth-corn collapse activity on chicken dorsal root ganglion cells as an indicator. As a result, one clone which did not exhibit any activity was found. The base sequencing of the clone revealed that aspartic acid residue at position 198 was substituted by glycine. When compared with other known animal Semaphorins, the regions before and after the position 198 were not markedly conserved, although the position corresponding to aspartic acid was highly conserved among Semaphorins with a few exceptions in which glutamic acid was located at that position. This suggested that the aspartic acid residue is essential to expression of the activity. The gene was then subjected to a site-directed mutagenesis by a conventional method to replace the glycine residue with aspartic acid. Since this mutagenesis restored the strong collapse activity, it was confirmed that all of the regions in the expression plasmid normally function except for that position. In conclusion, the aspartic acid at position 198 of Semaphorin III appears essential to expression of the Semaphorin function. The amino acid residues corresponding to the aspartic acid are aspartic acid at position 197 in the amino acid sequence of rat Semaphorin Y shown in SEQ ID NO: 3, and aspartic acid at position 198 in the amino acid sequence of human Semaphorin Y shown in SEQ ID NO: 6.

Reference Example 2

Tissue-specific Gene Expression of Semaphorin III Determined by Northern Analysis To determine the distribution of Semaphorin III gene expression among mouse tissues, RNAs were prepared from various adult mouse tissues, and subjected to Northern analysis. The procedures for preparation, blotting, and hybridization of RNA were the same as those described in Example 2. As a probe, the 560 bp MspI fragment of mouse Semaphorin III DNA described in Reference example 1 was used. As a result, it was demonstrated as shown in FIG. 5 that the expression of Semaphorin III in the adult is extremely high in the lung, while it is rather low in the CNS.

EFFECTS OF THE INVENTION

The present invention provides Semaphorin Y inhibiting neurite outgrowth, and a gene therefor, as well as other Semaphorins hybridizing to said Semaphorin Y gene, modified proteins or partial peptides of said Semaphorin Y, antibodies against said Semaphorin Y, antisense nucleotides against said Semaphorin Y gene, and the use of such substances as pharmaceutical or diagnostic agents or laboratory reagents. The present invention further provides a method of screening for Semaphorin Y antagonists employing said Semaphorin Y, Semaphorin Y antagonists obtained by said screening method, pharmaceutical agents comprising such antagonists, and transgenic animals involving said Semaphorin Y.

What is claimed is:

1. An isolated nucleic acid molecule comprising a polynucleotide having a nucleotide sequence selected from the group consisting of:
   (a) the nucleotide sequence of SEQ ID NO: 1,
   (b) the nucleotide sequence of SEQ ID NO: 2,
   (c) the nucleotide sequence of SEQ ID NO: 4,
   (d) the nucleotide sequence of SEQ ID NO: 5,
   (e) a cDNA sequence encoding the amino acid sequence of SEQ ID NO:3, and
   (f) a cDNA sequence encoding the amino acid sequence of SEQ ID NO: 6.

2. The isolated nucleic acid molecule of claim 1 that originates from a mammal.

3. A vector comprising the nucleic acid molecule of any one of claim 1 or 2.

4. A host cell comprising the vector of claim 3.

5. A process for producing a recombinant protein, comprising culturing the host cell of claim 4 under conditions sufficient for the production of said protein and recovering said protein.

6. An isolated polynucleotide comprising at least 18 contiguous nucleotides of the sequence of SEQ ID NO: 1 or SEQ ID NO: 4, with the proviso that said polynucleotide does not consist of at least 18 contiguous nucleotides of the sequence of the polynucleotide of GenBank Accession NO: R59527.

7. An isolated polynucleotide complementary to the polynucleotide of claim 6.

* * * * *

SEQUENCE LISTING

<160> NUMBER OF SEQ ID NOS: 13

<210> SEQ ID NO 1
<211> LENGTH: 3195
<212> TYPE: DNA
<213> ORGANISM: Rattus norvegicus
<220> FEATURE:
<221> NAME/KEY: misc_feature
<222> LOCATION: ()..()
<223> OTHER INFORMATION: Tissue Type: Brain
<221> NAME/KEY: 5'UTR
<222> LOCATION: (1)..(50)
<223> OTHER INFORMATION: Identification Method: E
<221> NAME/KEY: misc_feature
<222> LOCATION: (51)..(2837)
<223> OTHER INFORMATION: CDS;  Identification Method: E
<221> NAME/KEY: 3'UTR
<222> LOCATION: (2838)..(3195)
<223> OTHER INFORMATION: Identification Method: E

<400> SEQUENCE: 1

| | | | | | |
|---|---|---|---|---|---|
| gcggccgcgt | cgacgggta | ctccctgggg | cttgagctgc | ccgcacagg | atgccccgtg | 60 |
| cccccactc | catgcccttg | ctgctgctgt | tgctgctgtc | actccccaa | gcccagactg | 120 |
| cctttcccca | ggaccccatc | cctctgttga | cctctgacct | acaaggtacc | tctccgtcat | 180 |
| cctggttccg | gggcctggag | gacgatgctg | tggctgcgga | acttgggctg | gactttcaga | 240 |
| gattcctgac | cttgaaccgg | accttgcttg | tggctgcccg | ggatcacgtt | ttctccttcg | 300 |
| atcttcaagc | ccaagaagaa | gggagggggc | tggtgcccaa | caagtttctg | acatggcgga | 360 |
| gccaagacat | ggagaattgt | gctgtccggg | gaaagctgac | ggacgaatgc | tacaactaca | 420 |
| tccgtgttct | tgttccctgg | gactcgcaga | cactccttgc | ctgtggaaca | aattccttca | 480 |
| gccctgtgtg | tcgcagctat | gggataacat | ctctgcaaca | ggagggtgag | gagctgagtg | 540 |
| ggcaagctcg | atgccccttt | gatgccaccc | agtccactgt | ggccatctct | gcagagggta | 600 |
| gtttgtactc | agccacagca | gcagatttcc | aggccagtga | tgctgtggtt | tacagaagcc | 660 |
| ttggacctca | gcccccactc | cgttctgcaa | agtatgactc | caagtggctt | cgagagccac | 720 |
| actttgtcta | tgctttggag | catggagacc | atgtctactt | ctttcttccg | gagaagtctc | 780 |
| tgtggaggac | gcccggcctg | ggagggtgc | agttttcccg | ggtggcccgg | gtgtgtaaac | 840 |
| gtgacatggg | tggctcacca | cgggccttgg | atcgccactg | gacatccttc | cttaagctga | 900 |
| ggctcaactg | ctccgtccct | ggggactcta | ccttctactt | tgatgtctta | cagtccttaa | 960 |
| ctgggcctgt | gaacctgcat | gggcgctctg | ccctctttgg | ggtcttcact | actcagacca | 1020 |
| atagcattcc | tgggtctgca | gtctgcgcct | tctacctaga | tgacattgaa | cgtggctttg | 1080 |
| agggcaagtt | caaggagcag | aggagtctgg | atggggcctg | gactcctgtg | tctgaggaca | 1140 |
| aagtcccctc | acccaggcca | gggtcctgtg | caggtgtggg | tgcagctgcc | ttattctcct | 1200 |
| cctctcaaga | cctgcctgac | gatgtcctgc | tcttcatcaa | ggcacaccca | ctgctggatc | 1260 |
| ccgctgtgcc | acctgccacc | catcaacctc | tcctcactct | gactagcagg | gctctactga | 1320 |
| cccaggtagc | tgtggatggt | atggctggcc | cccacagaaa | tactacagtc | ctgtttcttg | 1380 |
| gctccaatga | tgggacagtg | ctgaaggtgc | tacctccagg | gggacagtct | ctgggacccg | 1440 |
| agcctatcat | attggaagag | attgatgcct | acagccatgc | ccggtgcagt | gggaagcggt | 1500 |
| cacccccgagc | tgctcgacgg | atcataggggc | tggagctgga | cactgagggt | cacaggcttt | 1560 |
| ttgtggcctt | tcctggatgc | atcgtctacc | tctctctcag | ccgctgtgcc | cggcatggag | 1620 |

-continued

```
catgtcagag gagctgcctg gcttctctgg acccatactg tggatggcat cggttccgag      1680
gctgtgtgaa tatcagggga cctggaggga ctgatgtgga tctgactggg aaccaggaat      1740
ccatggagca tggtgactgc caagatggag cgactgggag tcagtctggc cctggagatt      1800
ctgcctatgg cgtgcgcagg gacctttccc cagcctcagc ctcccgatcc atccccatcc      1860
cactcctcct ggcctgtgtg gcggcggcct tcgctttggg cgcctcagtc tccgcctct       1920 tggtgtcctg tgcttgtcgt cgcgcgaacc gccgtcggag caaggacatc gagaccccgg      1980
ggctgccgcg ccccctctcc cttcgcagtc tggcgaggct gcacggtggc ggtcctgagc      2040
ccccgcctcc gcccaaggat ggtgatgcag cgcaaacgcc cagctctac actaccttcc       2100 tgcctccgcc cgagggcgga tccccaccgg agctggcctg cctgcccacc ccggagacca      2160
cgcccgagct gccggtgaag cacctccgtg cctccggggg tccctgggag tggaaccaga      2220
acgggaacaa cgcttcggag ggcccaggcc gccacggggg ctgcagcgcg cgggcgggc       2280 ccgccccgcg cgtgctggtg aggccaccgc cccctggctg ccccgggcag gaggtggagg      2340
tgaccacgct ggaggaactg ctgcgctacc tgcacggccc gcagccgccc aggaagggca      2400
gcgaacctct cgcctccgcc ccgttcacct cccggccgcc tgcctcggag cccggcgccg      2460
ccttgttcgt ggactccagc ccgatgcctc gtgattgcgt gccgccgctg aggctcgacg      2520
taccgcccga cggcaagcgc gcggccccga gcgggcggcc tgctctctcg gccccggctc      2580
cacgcctggg cgtcagcggc agccgaagat tgcccttccc cacgcaccgg gcgcccccgg      2640
gcctgctcac ccgagtcccc tcgggaggcc cgtccaggta ctccggggg cccggagggc        2700 acctcctgta cctgggccgg cccgacggcc accgcggccg ctccctgaag agggtggacg      2760
tgaagtctcc actgtcgccc aaaccgcccc tcgccacacc gccgcagccc gccccgcacg      2820
gcagccattt taacttctga cagaagctgc tagcgcccgt cgaggcgctg gaggcctagg      2880
cctgcggagg ccgctggcct tcccggactc caagagtctc ccggggtccc ctctcgcctc      2940
ggtttattta ttgactgtct ttccccctgt cctttggcga ggagctcgcc gctcggagcg      3000
ccagcatttc aggggacctg gccgactccc actccccgct cccttccagc cacgctgcct      3060
taactcgtcg ctccggactc ccgcggactg ggccccgggc gggccggccg ggctggagc       3120 cgcgcgctgt gtacagagtc ctccggcctc ctggggccgg acgtgcctc ctcctactgt       3180 gtaggagccc ccacc                                                       3195
```

<210> SEQ ID NO 2
<211> LENGTH: 2787
<212> TYPE: DNA
<213> ORGANISM: Rattus norvegicus
<220> FEATURE:
<221> NAME/KEY: misc_feature
<222> LOCATION: ()..()
<223> OTHER INFORMATION: Tissue Type: Brain
<221> NAME/KEY: CDS
<222> LOCATION: (1)..(2787)
<223> OTHER INFORMATION: Identification Method: E
<221> NAME/KEY: misc_feature
<222> LOCATION: ()..()
<223> OTHER INFORMATION: Identification Method: P for resulting peptide

<400> SEQUENCE: 2

```
atg ccc cgt gcc ccc cac tcc atg ccc ttg ctg ctg ctg ttg ctg ctg        48
Met Pro Arg Ala Pro His Ser Met Pro Leu Leu Leu Leu Leu Leu Leu
1               5                   10                  15 tca ctc ccc caa gcc cag act gcc ttt ccc cag gac ccc atc cct ctg        96
Ser Leu Pro Gln Ala Gln Thr Ala Phe Pro Gln Asp Pro Ile Pro Leu
            20                  25                  30
```

-continued

| | |
|---|---|
| ttg acc tct gac cta caa ggt acc tct ccg tca tcc tgg ttc cgg ggc<br>Leu Thr Ser Asp Leu Gln Gly Thr Ser Pro Ser Ser Trp Phe Arg Gly<br>35                         40                       45 | 144 |
| ctg gag gac gat gct gtg gct gcg gaa ctt ggg ctg gac ttt cag aga<br>Leu Glu Asp Asp Ala Val Ala Ala Glu Leu Gly Leu Asp Phe Gln Arg<br>50                       55                     60 | 192 |
| ttc ctg acc ttg aac cgg acc ttg ctt gtg gct gcc cgg gat cac gtt<br>Phe Leu Thr Leu Asn Arg Thr Leu Leu Val Ala Ala Arg Asp His Val<br>65                      70                   75                 80 | 240 |
| ttc tcc ttc gat ctt caa gcc caa gaa gaa ggg gag ggg ctg gtg ccc<br>Phe Ser Phe Asp Leu Gln Ala Gln Glu Glu Gly Glu Gly Leu Val Pro<br>               85                     90                   95 | 288 |
| aac aag ttt ctg aca tgg cgg agc caa gac atg gag aat tgt gct gtc<br>Asn Lys Phe Leu Thr Trp Arg Ser Gln Asp Met Glu Asn Cys Ala Val<br>             100                   105                 110 | 336 |
| cgg gga aag ctg acg gac gaa tgc tac aac tac atc cgt gtt ctt gtt<br>Arg Gly Lys Leu Thr Asp Glu Cys Tyr Asn Tyr Ile Arg Val Leu Val<br>             115                   120                 125 | 384 |
| ccc tgg gac tcg cag aca ctc ctt gcc tgt gga aca aat tcc ttc agc<br>Pro Trp Asp Ser Gln Thr Leu Leu Ala Cys Gly Thr Asn Ser Phe Ser<br>             130                   135                 140 | 432 |
| cct gtg tgt cgc agc tat ggg ata aca tct ctg caa cag gag ggt gag<br>Pro Val Cys Arg Ser Tyr Gly Ile Thr Ser Leu Gln Gln Glu Gly Glu<br>145                     150                   155                 160 | 480 |
| gag ctg agt ggg caa gct cga tgc ccc ttt gat gcc acc cag tcc act<br>Glu Leu Ser Gly Gln Ala Arg Cys Pro Phe Asp Ala Thr Gln Ser Thr<br>             165                   170                 175 | 528 |
| gtg gcc atc tct gca gag ggt agt ttg tac tca gcc aca gca gca gat<br>Val Ala Ile Ser Ala Glu Gly Ser Leu Tyr Ser Ala Thr Ala Ala Asp<br>             180                   185                 190 | 576 |
| ttc cag gcc agt gat gct gtg gtt tac aga agc ctt gga cct cag ccc<br>Phe Gln Ala Ser Asp Ala Val Val Tyr Arg Ser Leu Gly Pro Gln Pro<br>             195                   200                 205 | 624 |
| cca ctc cgt tct gca aag tat gac tcc aag tgg ctt cga gag cca cac<br>Pro Leu Arg Ser Ala Lys Tyr Asp Ser Lys Trp Leu Arg Glu Pro His<br>210                     215                   220 | 672 |
| ttt gtc tat gct ttg gag cat gga gac cat gtc tac ttc ttt ctt ccg<br>Phe Val Tyr Ala Leu Glu His Gly Asp His Val Tyr Phe Phe Leu Pro<br>225                     230                   235                 240 | 720 |
| gag aag tct ctg tgg agg acg ccc ggc ctg ggg agg gtg cag ttt tcc<br>Glu Lys Ser Leu Trp Arg Thr Pro Gly Leu Gly Arg Val Gln Phe Ser<br>             245                   250                 255 | 768 |
| cgg gtg gcc cgg gtg tgt aaa cgt gac atg ggt ggc tca cca cgg gcc<br>Arg Val Ala Arg Val Cys Lys Arg Asp Met Gly Gly Ser Pro Arg Ala<br>             260                   265                 270 | 816 |
| ttg gat cgc cac tgg aca tcc ttc ctt aag ctg agg ctc aac tgc tcc<br>Leu Asp Arg His Trp Thr Ser Phe Leu Lys Leu Arg Leu Asn Cys Ser<br>             275                   280                 285 | 864 |
| gtc cct ggg gac tct acc ttc tac ttt gat gtc tta cag tcc tta act<br>Val Pro Gly Asp Ser Thr Phe Tyr Phe Asp Val Leu Gln Ser Leu Thr<br>             290                   295                 300 | 912 |
| ggg cct gtg aac ctg cat ggg cgc tct gcc ctc ttt ggg gtc ttc act<br>Gly Pro Val Asn Leu His Gly Arg Ser Ala Leu Phe Gly Val Phe Thr<br>305                     310                   315                 320 | 960 |
| act cag acc aat agc att cct ggg tct gca gtc tgc gcc ttc tac cta<br>Thr Gln Thr Asn Ser Ile Pro Gly Ser Ala Val Cys Ala Phe Tyr Leu<br>             325                   330                 335 | 1008 |
| gat gac att gaa cgt ggc ttt gag ggc aag ttc aag gag cag agg agt<br>Asp Asp Ile Glu Arg Gly Phe Glu Gly Lys Phe Lys Glu Gln Arg Ser | 1056 |

-continued

|  |  |  |  |  |  |  |  |  |  |  |  |  |  |  |  |  |
|---|---|---|---|---|---|---|---|---|---|---|---|---|---|---|---|---|
|  |  | 340 |  |  |  |  | 345 |  |  |  |  | 350 |  |  |  |  |
| ctg | gat | ggg | gcc | tgg | act | cct | gtg | tct | gag | gac | aaa | gtc | ccc | tca | ccc | 1104 |
| Leu | Asp | Gly | Ala | Trp | Thr | Pro | Val | Ser | Glu | Asp | Lys | Val | Pro | Ser | Pro |  |
|  |  | 355 |  |  |  |  | 360 |  |  |  |  | 365 |  |  |  |  |
| agg | cca | ggg | tcc | tgt | gca | ggt | gtg | ggt | gca | gct | gcc | tta | ttc | tcc | tcc | 1152 |
| Arg | Pro | Gly | Ser | Cys | Ala | Gly | Val | Gly | Ala | Ala | Ala | Leu | Phe | Ser | Ser |  |
|  |  | 370 |  |  |  |  | 375 |  |  |  |  | 380 |  |  |  |  |
| tct | caa | gac | ctg | cct | gac | gat | gtc | ctc | ttc | atc | aag | gca | cac | cca | | 1200 |
| Ser | Gln | Asp | Leu | Pro | Asp | Asp | Val | Leu | Phe | Ile | Lys | Ala | His | Pro | |  |
| 385 |  |  |  |  | 390 |  |  |  |  | 395 |  |  |  |  | 400 |  |
| ctg | ctg | gat | ccc | gct | gtg | cca | cct | gcc | acc | cat | caa | cct | ctc | ctc | act | 1248 |
| Leu | Leu | Asp | Pro | Ala | Val | Pro | Pro | Ala | Thr | His | Gln | Pro | Leu | Leu | Thr |  |
|  |  |  |  | 405 |  |  |  |  | 410 |  |  |  |  | 415 |  |  |
| ctg | act | agc | agg | gct | cta | ctg | acc | cag | gta | gct | gtg | gat | ggt | atg | gct | 1296 |
| Leu | Thr | Ser | Arg | Ala | Leu | Leu | Thr | Gln | Val | Ala | Val | Asp | Gly | Met | Ala |  |
|  |  |  |  | 420 |  |  |  |  | 425 |  |  |  |  | 430 |  |  |
| ggc | ccc | cac | aga | aat | act | aca | gtc | ctg | ttt | ctt | ggc | tcc | aat | gat | ggg | 1344 |
| Gly | Pro | His | Arg | Asn | Thr | Thr | Val | Leu | Phe | Leu | Gly | Ser | Asn | Asp | Gly |  |
|  |  |  | 435 |  |  |  |  | 440 |  |  |  |  | 445 |  |  |  |
| aca | gtg | ctg | aag | gtg | cta | cct | cca | ggg | gga | cag | tct | ctg | gga | ccc | gag | 1392 |
| Thr | Val | Leu | Lys | Val | Leu | Pro | Pro | Gly | Gly | Gln | Ser | Leu | Gly | Pro | Glu |  |
|  |  | 450 |  |  |  |  | 455 |  |  |  |  | 460 |  |  |  |  |
| cct | atc | ata | ttg | gaa | gag | att | gat | gcc | tac | agc | cat | gcc | cgg | tgc | agt | 1440 |
| Pro | Ile | Ile | Leu | Glu | Glu | Ile | Asp | Ala | Tyr | Ser | His | Ala | Arg | Cys | Ser |  |
| 465 |  |  |  |  | 470 |  |  |  |  | 475 |  |  |  |  | 480 |  |
| ggg | aag | cgg | tca | ccc | cga | gct | gcc | cga | cgg | atc | ata | ggg | ctg | gag | ctg | 1488 |
| Gly | Lys | Arg | Ser | Pro | Arg | Ala | Ala | Arg | Arg | Ile | Ile | Gly | Leu | Glu | Leu |  |
|  |  |  |  | 485 |  |  |  |  | 490 |  |  |  |  | 495 |  |  |
| gac | act | gag | ggt | cac | agg | ctt | ttt | gtg | gcc | ttt | cct | gga | tgc | atc | gtc | 1536 |
| Asp | Thr | Glu | Gly | His | Arg | Leu | Phe | Val | Ala | Phe | Pro | Gly | Cys | Ile | Val |  |
|  |  |  |  | 500 |  |  |  |  | 505 |  |  |  |  | 510 |  |  |
| tac | ctc | tct | ctc | agc | cgc | tgt | gcc | cgg | cat | gga | gca | tgt | cag | agg | agc | 1584 |
| Tyr | Leu | Ser | Leu | Ser | Arg | Cys | Ala | Arg | His | Gly | Ala | Cys | Gln | Arg | Ser |  |
|  |  |  | 515 |  |  |  |  | 520 |  |  |  |  | 525 |  |  |  |
| tgc | ctg | gct | tct | ctg | gac | cca | tac | tgt | gga | tgg | cat | cgg | ttc | cga | ggc | 1632 |
| Cys | Leu | Ala | Ser | Leu | Asp | Pro | Tyr | Cys | Gly | Trp | His | Arg | Phe | Arg | Gly |  |
|  |  | 530 |  |  |  |  | 535 |  |  |  |  | 540 |  |  |  |  |
| tgt | gtg | aat | atc | agg | gga | cct | gga | ggg | act | gat | gtg | gat | ctg | act | ggg | 1680 |
| Cys | Val | Asn | Ile | Arg | Gly | Pro | Gly | Gly | Thr | Asp | Val | Asp | Leu | Thr | Gly |  |
| 545 |  |  |  |  | 550 |  |  |  |  | 555 |  |  |  |  | 560 |  |
| aac | cag | gaa | tcc | atg | gag | cat | ggt | gac | tgc | caa | gat | gga | gcg | act | ggg | 1728 |
| Asn | Gln | Glu | Ser | Met | Glu | His | Gly | Asp | Cys | Gln | Asp | Gly | Ala | Thr | Gly |  |
|  |  |  |  | 565 |  |  |  |  | 570 |  |  |  |  | 575 |  |  |
| agt | cag | tct | ggc | cct | gga | gat | tct | gcc | tat | ggc | gtg | cgc | agg | gac | ctt | 1776 |
| Ser | Gln | Ser | Gly | Pro | Gly | Asp | Ser | Ala | Tyr | Gly | Val | Arg | Arg | Asp | Leu |  |
|  |  |  | 580 |  |  |  |  | 585 |  |  |  |  | 590 |  |  |  |
| tcc | cca | gcc | tca | gcc | tcc | cga | tcc | atc | ccc | atc | cca | ctc | ctc | ctg | gcc | 1824 |
| Ser | Pro | Ala | Ser | Ala | Ser | Arg | Ser | Ile | Pro | Ile | Pro | Leu | Leu | Leu | Ala |  |
|  |  | 595 |  |  |  |  | 600 |  |  |  |  | 605 |  |  |  |  |
| tgt | gtg | gcg | gcg | gcc | ttc | gct | ttg | ggc | gcc | tca | gtc | tcc | ggc | ctc | ttg | 1872 |
| Cys | Val | Ala | Ala | Ala | Phe | Ala | Leu | Gly | Ala | Ser | Val | Ser | Gly | Leu | Leu |  |
|  |  | 610 |  |  |  |  | 615 |  |  |  |  | 620 |  |  |  |  |
| gtg | tcc | tgt | gct | tgt | cgt | cgc | gcg | aac | cgc | cgt | cgg | agc | aag | gac | atc | 1920 |
| Val | Ser | Cys | Ala | Cys | Arg | Arg | Ala | Asn | Arg | Arg | Arg | Ser | Lys | Asp | Ile |  |
| 625 |  |  |  |  | 630 |  |  |  |  | 635 |  |  |  |  | 640 |  |
| gag | acc | ccg | ggg | ctg | ccg | cgc | ccc | ctc | tcc | ctt | cgc | agt | ctg | gcg | agg | 1968 |
| Glu | Thr | Pro | Gly | Leu | Pro | Arg | Pro | Leu | Ser | Leu | Arg | Ser | Leu | Ala | Arg |  |
|  |  |  |  | 645 |  |  |  |  | 650 |  |  |  |  | 655 |  |  |
| ctg | cac | ggt | ggc | ggt | cct | gag | ccc | ccg | cct | ccg | ccc | aag | gat | ggt | gat | 2016 |

```
                                                              -continued

Leu His Gly Gly Gly Pro Glu Pro Pro Pro Pro Lys Asp Gly Asp
            660                 665                 670 gca gcg caa acg ccc cag ctc tac act acc ttc ctg cct ccg ccc gag      2064
Ala Ala Gln Thr Pro Gln Leu Tyr Thr Thr Phe Leu Pro Pro Pro Glu
        675                 680                 685 ggc gga tcc cca ccg gag ctg gcc tgc ctg ccc acc ccg gag acc acg      2112
Gly Gly Ser Pro Pro Glu Leu Ala Cys Leu Pro Thr Pro Glu Thr Thr
690                 695                 700 ccc gag ctg ccg gtg aag cac ctc cgt gcc tcc ggg ggt ccc tgg gag      2160
Pro Glu Leu Pro Val Lys His Leu Arg Ala Ser Gly Gly Pro Trp Glu
705                 710                 715                 720 tgg aac cag aac ggg aac aac gct tcg gag ggc cca ggc cgc cca cgg      2208
Trp Asn Gln Asn Gly Asn Asn Ala Ser Glu Gly Pro Gly Arg Pro Arg
                725                 730                 735 ggc tgc agc gcg gcg ggc ggg ccc gcc ccg cgc gtg ctg gtg agg cca      2256
Gly Cys Ser Ala Ala Gly Gly Pro Ala Pro Arg Val Leu Val Arg Pro
            740                 745                 750 ccg ccc cct ggc tgc ccc ggg cag gag gtg gag gtg acc acg ctg gag      2304
Pro Pro Pro Gly Cys Pro Gly Gln Glu Val Glu Val Thr Thr Leu Glu
        755                 760                 765 gaa ctg ctg cgc tac ctg cac ggc ccg cag ccg ccc agg aag ggc agc      2352
Glu Leu Leu Arg Tyr Leu His Gly Pro Gln Pro Pro Arg Lys Gly Ser
770                 775                 780 gaa cct ctc gcc tcc gcc ccg ttc acc tcc cgg ccg cct gcc tcg gag      2400
Glu Pro Leu Ala Ser Ala Pro Phe Thr Ser Arg Pro Pro Ala Ser Glu
785                 790                 795                 800 ccc ggc gcc gcc ttg ttc gtg gac tcc agc ccg atg cct cgt gat tgc      2448
Pro Gly Ala Ala Leu Phe Val Asp Ser Ser Pro Met Pro Arg Asp Cys
                805                 810                 815 gtg ccg ccg ctg agg ctc gac gta ccg ccc gac ggc aag cgc gcg gcc      2496
Val Pro Pro Leu Arg Leu Asp Val Pro Pro Asp Gly Lys Arg Ala Ala
            820                 825                 830 ccg agc ggg cgg cct gct ctc tcg gcc ccg gct cca cgc ctg ggc gtc      2544
Pro Ser Gly Arg Pro Ala Leu Ser Ala Pro Ala Pro Arg Leu Gly Val
        835                 840                 845 agc ggc agc cga aga ttg ccc ttc ccc acg cac cgg gcg ccc ccg ggc      2592
Ser Gly Ser Arg Arg Leu Pro Phe Pro Thr His Arg Ala Pro Pro Gly
850                 855                 860 ctg ctc acc cga gtc ccc tcg gga ggc ccg tca ggg tac tcc ggg ggg      2640
Leu Leu Thr Arg Val Pro Ser Gly Gly Pro Ser Arg Tyr Ser Gly Gly
865                 870                 875                 880 ccc ggg agg cac ctc ctg tac ctg ggc cgg ccc gac ggc cac cgc ggc      2688
Pro Gly Arg His Leu Leu Tyr Leu Gly Arg Pro Asp Gly His Arg Gly
                885                 890                 895 cgc tcc ctg aag agg gtg gac gtg aag tct cca ctg tcg ccc aaa ccg      2736
Arg Ser Leu Lys Arg Val Asp Val Lys Ser Pro Leu Ser Pro Lys Pro
            900                 905                 910 ccc ctc gcc aca ccg ccg cag ccc gcc ccg cac ggc agc cat ttt aac      2784
Pro Leu Ala Thr Pro Pro Gln Pro Ala Pro His Gly Ser His Phe Asn
        915                 920                 925 ttc                                                                   2787
Phe

<210> SEQ ID NO 3
<211> LENGTH: 929
<212> TYPE: PRT
<213> ORGANISM: Rattus norvegicus
<220> FEATURE:
<221> NAME/KEY: misc_feature
<222> LOCATION: ()..()
<223> OTHER INFORMATION: Tissue Type: Brain
```

-continued

```
<221> NAME/KEY: misc_feature
<222> LOCATION: ()..()
<223> OTHER INFORMATION: Identification Method: P for resulting peptide

<400> SEQUENCE: 3
```

Met Pro Arg Ala Pro His Ser Met Pro Leu Leu Leu Leu Leu Leu
1               5                   10                  15

Ser Leu Pro Gln Ala Gln Thr Ala Phe Pro Gln Asp Pro Ile Pro Leu
            20                  25                  30

Leu Thr Ser Asp Leu Gln Gly Thr Ser Pro Ser Ser Trp Phe Arg Gly
        35                  40                  45

Leu Glu Asp Asp Ala Val Ala Ala Glu Leu Gly Leu Asp Phe Gln Arg
    50                  55                  60

Phe Leu Thr Leu Asn Arg Thr Leu Leu Val Ala Ala Arg Asp His Val
65                  70                  75                  80

Phe Ser Phe Asp Leu Gln Ala Gln Glu Glu Gly Glu Gly Leu Val Pro
                85                  90                  95

Asn Lys Phe Leu Thr Trp Arg Ser Gln Asp Met Glu Asn Cys Ala Val
            100                 105                 110

Arg Gly Lys Leu Thr Asp Glu Cys Tyr Asn Tyr Ile Arg Val Leu Val
        115                 120                 125

Pro Trp Asp Ser Gln Thr Leu Leu Ala Cys Gly Thr Asn Ser Phe Ser
    130                 135                 140

Pro Val Cys Arg Ser Tyr Gly Ile Thr Ser Leu Gln Gln Glu Gly Glu
145                 150                 155                 160

Glu Leu Ser Gly Gln Ala Arg Cys Pro Phe Asp Ala Thr Gln Ser Thr
                165                 170                 175

Val Ala Ile Ser Ala Glu Gly Ser Leu Tyr Ser Ala Thr Ala Ala Asp
            180                 185                 190

Phe Gln Ala Ser Asp Ala Val Val Tyr Arg Ser Leu Gly Pro Gln Pro
        195                 200                 205

Pro Leu Arg Ser Ala Lys Tyr Asp Ser Lys Trp Leu Arg Glu Pro His
    210                 215                 220

Phe Val Tyr Ala Leu Glu His Gly Asp His Val Tyr Phe Phe Leu Pro
225                 230                 235                 240

Glu Lys Ser Leu Trp Arg Thr Pro Gly Leu Gly Arg Val Gln Phe Ser
                245                 250                 255

Arg Val Ala Arg Val Cys Lys Arg Asp Met Gly Gly Ser Pro Arg Ala
            260                 265                 270

Leu Asp Arg His Trp Thr Ser Phe Leu Lys Leu Arg Leu Asn Cys Ser
        275                 280                 285

Val Pro Gly Asp Ser Thr Phe Tyr Phe Asp Val Leu Gln Ser Leu Thr
    290                 295                 300

Gly Pro Val Asn Leu His Gly Arg Ser Ala Leu Phe Gly Val Phe Thr
305                 310                 315                 320

Thr Gln Thr Asn Ser Ile Pro Gly Ser Ala Val Cys Ala Phe Tyr Leu
                325                 330                 335

Asp Asp Ile Glu Arg Gly Phe Glu Gly Lys Phe Lys Glu Gln Arg Ser
            340                 345                 350

Leu Asp Gly Ala Trp Thr Pro Val Ser Glu Asp Lys Val Pro Ser Pro
        355                 360                 365

Arg Pro Gly Ser Cys Ala Gly Val Gly Ala Ala Leu Phe Ser Ser
    370                 375                 380

Ser Gln Asp Leu Pro Asp Asp Val Leu Leu Phe Ile Lys Ala His Pro

-continued

```
            385                 390                 395                 400
Leu Leu Asp Pro Ala Val Pro Pro Ala Thr His Gln Pro Leu Leu Thr
                405                 410                 415
Leu Thr Ser Arg Ala Leu Leu Thr Gln Val Ala Val Asp Gly Met Ala
                420                 425                 430
Gly Pro His Arg Asn Thr Thr Val Leu Phe Leu Gly Ser Asn Asp Gly
                435                 440                 445
Thr Val Leu Lys Val Leu Pro Pro Gly Gly Gln Ser Leu Gly Pro Glu
            450                 455                 460
Pro Ile Ile Leu Glu Glu Ile Asp Ala Tyr Ser His Ala Arg Cys Ser
465                 470                 475                 480
Gly Lys Arg Ser Pro Arg Ala Ala Arg Arg Ile Ile Gly Leu Glu Leu
                485                 490                 495
Asp Thr Glu Gly His Arg Leu Phe Val Ala Phe Pro Gly Cys Ile Val
                500                 505                 510
Tyr Leu Ser Leu Ser Arg Cys Ala Arg His Gly Ala Cys Gln Arg Ser
            515                 520                 525
Cys Leu Ala Ser Leu Asp Pro Tyr Cys Gly Trp His Arg Phe Arg Gly
            530                 535                 540
Cys Val Asn Ile Arg Gly Pro Gly Gly Thr Asp Val Asp Leu Thr Gly
545                 550                 555                 560
Asn Gln Glu Ser Met Glu His Gly Asp Cys Gln Asp Gly Ala Thr Gly
                565                 570                 575
Ser Gln Ser Gly Pro Gly Asp Ser Ala Tyr Gly Val Arg Arg Asp Leu
            580                 585                 590
Ser Pro Ala Ser Ala Ser Arg Ser Ile Pro Ile Pro Leu Leu Leu Ala
            595                 600                 605
Cys Val Ala Ala Ala Phe Ala Leu Gly Ala Ser Val Ser Gly Leu Leu
            610                 615                 620
Val Ser Cys Ala Cys Arg Arg Ala Asn Arg Arg Arg Ser Lys Asp Ile
625                 630                 635                 640
Glu Thr Pro Gly Leu Pro Arg Pro Leu Ser Leu Arg Ser Leu Ala Arg
                645                 650                 655
Leu His Gly Gly Gly Pro Glu Pro Pro Pro Pro Lys Asp Gly Asp
                660                 665                 670
Ala Ala Gln Thr Pro Gln Leu Tyr Thr Thr Phe Leu Pro Pro Pro Glu
            675                 680                 685
Gly Gly Ser Pro Pro Glu Leu Ala Cys Leu Pro Thr Pro Glu Thr Thr
            690                 695                 700
Pro Glu Leu Pro Val Lys His Leu Arg Ala Ser Gly Gly Pro Trp Glu
705                 710                 715                 720
Trp Asn Gln Asn Gly Asn Asn Ala Ser Glu Gly Pro Gly Arg Pro Arg
                725                 730                 735
Gly Cys Ser Ala Ala Gly Gly Pro Ala Pro Arg Val Leu Val Arg Pro
                740                 745                 750
Pro Pro Pro Gly Cys Pro Gly Gln Glu Val Glu Val Thr Thr Leu Glu
            755                 760                 765
Glu Leu Leu Arg Tyr Leu His Gly Pro Gln Pro Pro Arg Lys Gly Ser
            770                 775                 780
Glu Pro Leu Ala Ser Ala Pro Phe Thr Ser Arg Pro Pro Ala Ser Glu
785                 790                 795                 800
Pro Gly Ala Ala Leu Phe Val Asp Ser Ser Pro Met Pro Arg Asp Cys
                805                 810                 815
```

```
Val Pro Pro Leu Arg Leu Asp Val Pro Asp Gly Lys Arg Ala Ala
        820                 825                 830

Pro Ser Gly Arg Pro Ala Leu Ser Ala Pro Ala Pro Arg Leu Gly Val
        835                 840                 845

Ser Gly Ser Arg Arg Leu Pro Phe Pro Thr His Arg Ala Pro Pro Gly
        850                 855                 860

Leu Leu Thr Arg Val Pro Ser Gly Pro Ser Arg Tyr Ser Gly Gly
865                 870                 875                 880

Pro Gly Arg His Leu Leu Tyr Leu Gly Arg Pro Asp Gly His Arg Gly
                885                 890                 895

Arg Ser Leu Lys Arg Val Asp Val Lys Ser Pro Leu Ser Pro Lys Pro
        900                 905                 910

Pro Leu Ala Thr Pro Pro Gln Pro Ala Pro His Gly Ser His Phe Asn
        915                 920                 925

Phe

<210> SEQ ID NO 4
<211> LENGTH: 3432
<212> TYPE: DNA
<213> ORGANISM: Homo sapiens
<220> FEATURE:
<221> NAME/KEY: misc_feature
<222> LOCATION: ()..()
<223> OTHER INFORMATION: Tissue Type: Child Brain
<221> NAME/KEY: 5'UTR
<222> LOCATION: (1)..(187)
<223> OTHER INFORMATION: Identification Method: E
<221> NAME/KEY: misc_feature
<222> LOCATION: (188)..(2977)
<223> OTHER INFORMATION: CDS; Identification Method: E
<221> NAME/KEY: 3'UTR
<222> LOCATION: (2978)..(3407)
<223> OTHER INFORMATION: Identification Method: E
<221> NAME/KEY: polyA_signal
<222> LOCATION: (3408)..(3432)
<223> OTHER INFORMATION: Identification Method: E

<400> SEQUENCE: 4
aaaaccacgg attgcgaact cagcgcagcg cgtggccgct ggccgcccgc ggcgatctcg      60
atcccgctga cccgaatcct ggagtcagag gtttcctatc cccctcaagc ccccacagga    120
gtcaccaacc cagggccggc ttatgggtga gggggcaccc cctggggcct gagctgcccc    180
acacaggatg ccccgtgccc cccacttcat gccttgctg ctactgctgc tgctgctctc     240
acttccccat actcaggccg ccttttcccca ggaccccctc cctctgttga tctctgacct    300
tcaaggtact tccccattat cctggtttcg gggcctggag gatgatgctg tggctgcaga    360
acttgggctg gactttcaga gattcctgac cttgaaccgg accttgctag tggctgcccg    420
ggatcacgtt ttctccttcg atcttcaagc cgaagaagaa ggggaggggc tggtgcccaa    480
caagtatcta acatggagaa gccaagatgt ggagaactgt gctgtacggg gaaagctgac    540
ggatgagtgc tacaactata ttcgtgttct tgttccctgg gactcccaga cgctccttgc    600
ctgtggaacg aactcattca gccctgtgtg ccgcagctat gggataactt cgctgcagca    660
ggagggtgag gaactgagtg ggcaggctcg atgcccccttt gatgccaccc agtccaacgt    720
ggccatcttt gcagagggca gcctgtactc agccacagct gcggatttcc aggccagtga    780
tgctgtagtt tacagaagcc ttgggcccca gccccactc cgctccgcca agtatgactc     840
caagtggctc cgagagccac actttgtcca ggccttggag catggagacc atgtctactt    900
cttcttccgc gaggtctctg tggaggatgc tcggctgggg aaggtgcagt tctcccgcgt    960
```

-continued

```
agcccgagta tgtaaacgtg acatgggcgg ctcgcctcgg gccttggacc gccactggac   1020
atccttcctg aagcttcggc tcaactgctc tgtccctggg gactctactt tctattttga   1080
tgttttacag gccttgactg ggcctgtgaa cctgcatggc cgctctgctc tctttggggt   1140
cttcaccacc cagaccaata gcatccctg ctctgccgtc tgcgccttct acctggatga   1200
gattgagcgt gggtttgagg gcaagttcaa ggagcagagg agtctggatg gggcctggac   1260
tcctgtgtct gaggacagag ttccctcacc caggccagga tcctgtgcag gagtagggg    1320 agctgccttg ttctcctctt cccgagacct ccctgatgat gtcctgacct tcatcaaggc   1380
tcacccgctg ctggaccccg ctgtaccacc tgtcacccat cagcctctac tcactctcac   1440
tagcagggcc ctactgaccc aagtagctgt ggatggcatg gctggtcccc acagtaacat   1500
cacagtcatg ttccttggct ccaatgatgg gacagtgctg aaggtgctga ccccaggtgg   1560
gcgatccggg ggacctgagc ccatcctcct ggaagagatt gatgcctaca gccctgcccg   1620
gtgcagtggg aagcggacag cccaaacagc acgacggatc atagggctgg agctggacac   1680
tgagggtcac aggcttttg tggctttttc tggctgtatt gtctacctcc ctctcagccg    1740
gtgtgcccgg catggggcct gtcagaggag ctgtttggct tctcaggacc catactgtgg   1800
atggcatagc tccagggct gtgtggatat caggggatct ggtgggactg atgtggatca    1860
ggctgggaac caggaatcca tggagcatgg tgactgccaa gatggagcta ctgggagtca   1920
gtctggccct gggattctg cttatggcgt gcgccggggac ctgcccccag cctcggcctc    1980
ccgctccgtc cccatcccac tcctcctggc cagtgtggcc gcagcttttg ccctgggcgc   2040
ctcagtctct ggcctcctgg tctcctgtgc ttgtcgccgc gcccaccgac gtcggggcaa   2100
ggacatcgag actcccgggc tcccgcgccc tctctccctc cgcagtttgg cccggctcca   2160
cggtgggggc ccagagcccc cgccgccctc aaggacgggg acgcggtgc agacgccgca    2220 gctctacacc accttcctgc cgcctccgga gggcgtgccc ccgccggagc tggcctgcct   2280
gcccaccccc gagtccacgc cggagctgcc ggtcaagcac ctccgcgccg ccggggaccc   2340
ctgggagtgg aaccagaaca ggaacaacgc caaggagggt ccgggccgct cacggggcgg   2400
gcacgcggcg ggcgggcccg cgcccgcgt gctggtgagg ccaccgccgc ccggctgtcc    2460
cgggcaggcc gtggaagtca ccaccctgga ggaactgctg cgctacctgc acggcccgca   2520
gccgcccaga aaggggggccg agccccccgc cccttttaacc tcgcgggcgc tcccgccgga   2580
gcccgccccc gccctcttgg gcggccccag ccccaggccc cacgagtgcg cctcgccgct   2640
gaggctggac gtgcccccc agggcaggtg cgcctctgcc ccgcccggc ccgcgctctc     2700 cgccccccgct cccccggctgg gcgtcggcgg aggccggagg ttgcctttct ccggccaccg   2760 ggcccccccct gccctgctca ctcgagtccc ctcgggaggt ccctccaggt actccgggg    2820 tcccgggaag cacctcctgt acctgggccg gcccgagggc taccggggcc gcgccctgaa   2880
aagggtggac gtcgagaagc cccagttgtc cctgaagcct cccctcgtcg ggccctcctc   2940
ccgccaggcc gtcccgaacg gcggccgttt caacttttaa agggagcggt ccacggcctc   3000
cagcgtgggg agcgcccgag tcctctcggt cacgagctgg acgctcttca ggacgttca    3060 ccgcccccctc gccccgcacc tccagccttc ccgactcgca gagtctcccg aggccccttt    3120
tcgcctcggg tttatttatt gactgtcttt cccctgtcc tcgacagaag agtgggaggt    3180
gagaagcccg tctcctcagt gagccagcat tcaggggga gctggcggac tcccactccc    3240
cgctcccttc cagccaagct gccttaactc gccctcggg gctcccccag agactgtgcc    3300
```

```
ccgggcgggc cgcgcgcgct gtgtccagag tcctcgggcc tcctgggtct ggacgtgcc    3360 tctcctactg tgtaggagcc tccgcttccc aatacagccg tgtctgcaaa aaaaaaaaa    3420 aaaaaaaaaa aa                                                       3432

<210> SEQ ID NO 5
<211> LENGTH: 2790
<212> TYPE: DNA
<213> ORGANISM: Homo sapiens
<220> FEATURE:
<221> NAME/KEY: misc_feature
<222> LOCATION: ()..()
<223> OTHER INFORMATION: Tissue Type: Child Brain
<221> NAME/KEY: CDS
<222> LOCATION: (1)..(2790)
<223> OTHER INFORMATION: Identification Method: E
<221> NAME/KEY: misc_feature
<222> LOCATION: ()..()
<223> OTHER INFORMATION: Identification Method: P for resulting peptide

<400> SEQUENCE: 5 atg ccc cgt gcc ccc cac ttc atg ccc ttg ctg cta ctg ctg ctg ctg     48
Met Pro Arg Ala Pro His Phe Met Pro Leu Leu Leu Leu Leu Leu Leu
1               5                   10                  15 ctc tca ctt ccc cat act cag gcc gcc ttt ccc cag gac ccc ctc cct     96
Leu Ser Leu Pro His Thr Gln Ala Ala Phe Pro Gln Asp Pro Leu Pro
            20                  25                  30 ctg ttg atc tct gac ctt caa ggt act tcc cca tta tcc tgg ttt cgg    144
Leu Leu Ile Ser Asp Leu Gln Gly Thr Ser Pro Leu Ser Trp Phe Arg
        35                  40                  45 ggc ctg gag gat gat gct gtg gct gca gaa ctt ggg ctg gac ttt cag    192
Gly Leu Glu Asp Asp Ala Val Ala Ala Glu Leu Gly Leu Asp Phe Gln
50                  55                  60 aga ttc ctg acc ttg aac cgg acc ttg cta gtg gct gcc cgg gat cac    240
Arg Phe Leu Thr Leu Asn Arg Thr Leu Leu Val Ala Ala Arg Asp His
65                  70                  75                  80 gtt ttc tcc ttc gat ctt caa gcc gaa gaa gaa ggg gag ggg ctg gtg    288
Val Phe Ser Phe Asp Leu Gln Ala Glu Glu Glu Gly Glu Gly Leu Val
                85                  90                  95 ccc aac aag tat cta aca tgg aga agc caa gat gtg gag aac tgt gct    336
Pro Asn Lys Tyr Leu Thr Trp Arg Ser Gln Asp Val Glu Asn Cys Ala
            100                 105                 110 gta cgg gga aag ctg acg gat gag tgc tac aac tat att cgt gtt ctt    384
Val Arg Gly Lys Leu Thr Asp Glu Cys Tyr Asn Tyr Ile Arg Val Leu
        115                 120                 125 gtt ccc tgg gac tcc cag acg ctc ctt gcc tgt gga acg aac tca ttc    432
Val Pro Trp Asp Ser Gln Thr Leu Leu Ala Cys Gly Thr Asn Ser Phe
    130                 135                 140 agc cct gtg tgc cgc agc tat ggg ata act tcg ctg cag cag gag ggt    480
Ser Pro Val Cys Arg Ser Tyr Gly Ile Thr Ser Leu Gln Gln Glu Gly
145                 150                 155                 160 gag gaa ctg agt ggg cag gct cga tgc ccc ttt gat gcc acc cag tcc    528
Glu Glu Leu Ser Gly Gln Ala Arg Cys Pro Phe Asp Ala Thr Gln Ser
                165                 170                 175 aac gtg gcc atc ttt gca gag ggc agc ctg tac tca gcc aca gct gcg    576
Asn Val Ala Ile Phe Ala Glu Gly Ser Leu Tyr Ser Ala Thr Ala Ala
            180                 185                 190 gat ttc cag gcc agt gat gct gta gtt tac aga agc ctt ggg ccc cag    624
Asp Phe Gln Ala Ser Asp Ala Val Val Tyr Arg Ser Leu Gly Pro Gln
        195                 200                 205 ccc cca ctc cgc tcc gcc aag tat gac tcc aag tgg ctc cga gag cca    672
Pro Pro Leu Arg Ser Ala Lys Tyr Asp Ser Lys Trp Leu Arg Glu Pro
    210                 215                 220
```

-continued

```
cac ttt gtc cag gcc ttg gag cat gga gac cat gtc tac ttc ttc ttc      720
His Phe Val Gln Ala Leu Glu His Gly Asp His Val Tyr Phe Phe Phe
225                 230                 235                 240 cgc gag gtc tct gtg gag gat gct cgg ctg ggg aag gtg cag ttc tcc      768
Arg Glu Val Ser Val Glu Asp Ala Arg Leu Gly Lys Val Gln Phe Ser
                245                 250                 255 cgc gta gcc cga gta tgt aaa cgt gac atg ggc ggc tcg cct cgg gcc      816
Arg Val Ala Arg Val Cys Lys Arg Asp Met Gly Gly Ser Pro Arg Ala
            260                 265                 270 ttg gac cgc cac tgg aca tcc ttc ctg aag ctt cgg ctc aac tgc tct      864
Leu Asp Arg His Trp Thr Ser Phe Leu Lys Leu Arg Leu Asn Cys Ser
        275                 280                 285 gtc cct ggg gac tct act ttc tat ttt gat gtt tta cag gcc ttg act      912
Val Pro Gly Asp Ser Thr Phe Tyr Phe Asp Val Leu Gln Ala Leu Thr
    290                 295                 300 ggg cct gtg aac ctg cat ggc cgc tct gct ctc ttt ggg gtc ttc acc      960
Gly Pro Val Asn Leu His Gly Arg Ser Ala Leu Phe Gly Val Phe Thr
305                 310                 315                 320 acc cag acc aat agc atc cct ggc tct gcc gtc tgc gcc ttc tac ctg     1008
Thr Gln Thr Asn Ser Ile Pro Gly Ser Ala Val Cys Ala Phe Tyr Leu
                325                 330                 335 gat gag att gag cgt ggg ttt gag ggc aag ttc aag gag cag agg agt     1056
Asp Glu Ile Glu Arg Gly Phe Glu Gly Lys Phe Lys Glu Gln Arg Ser
            340                 345                 350 ctg gat ggg gcc tgg act cct gtg tct gag gac aga gtt ccc tca ccc     1104
Leu Asp Gly Ala Trp Thr Pro Val Ser Glu Asp Arg Val Pro Ser Pro
        355                 360                 365 agg cca gga tcc tgt gca gga gta ggg gga gct gcc ttg ttc tcc tct     1152
Arg Pro Gly Ser Cys Ala Gly Val Gly Gly Ala Ala Leu Phe Ser Ser
    370                 375                 380 tcc cga gac ctc cct gat gat gtc ctg acc ttc atc aag gct cac ccg     1200
Ser Arg Asp Leu Pro Asp Asp Val Leu Thr Phe Ile Lys Ala His Pro
385                 390                 395                 400 ctg ctg gac ccc gct gta cca cct gtc acc cat cag cct cta ctc act     1248
Leu Leu Asp Pro Ala Val Pro Pro Val Thr His Gln Pro Leu Leu Thr
                405                 410                 415 ctc act agc agg gcc cta ctg acc caa gta gct gtg gat ggc atg gct     1296
Leu Thr Ser Arg Ala Leu Leu Thr Gln Val Ala Val Asp Gly Met Ala
            420                 425                 430 ggt ccc cac agt aac atc aca gtc atg ttc ctt ggc tcc aat gat ggg     1344
Gly Pro His Ser Asn Ile Thr Val Met Phe Leu Gly Ser Asn Asp Gly
        435                 440                 445 aca gtg ctg aag gtg ctg acc cca ggt ggg cga tcc ggg gga cct gag     1392
Thr Val Leu Lys Val Leu Thr Pro Gly Gly Arg Ser Gly Gly Pro Glu
    450                 455                 460 ccc atc ctc ctg gaa gag att gat gcc tac agc cct gcc cgg tgc agt     1440
Pro Ile Leu Leu Glu Glu Ile Asp Ala Tyr Ser Pro Ala Arg Cys Ser
465                 470                 475                 480 ggg aag cgg aca gcc caa aca gca cga cgg atc ata ggg ctg gag ctg     1488
Gly Lys Arg Thr Ala Gln Thr Ala Arg Arg Ile Ile Gly Leu Glu Leu
                485                 490                 495 gac act gag ggt cac agg ctt ttt gtg gct ttt tct ggc tgt att gtc     1536
Asp Thr Glu Gly His Arg Leu Phe Val Ala Phe Ser Gly Cys Ile Val
            500                 505                 510 tac ctc cct ctc agc cgg tgt gcc cgg cat ggg gcc tgt cag agg agc     1584
Tyr Leu Pro Leu Ser Arg Cys Ala Arg His Gly Ala Cys Gln Arg Ser
        515                 520                 525 tgt ttg gct tct cag gac cca tac tgt gga tgg cat agc tcc agg ggc     1632
Cys Leu Ala Ser Gln Asp Pro Tyr Cys Gly Trp His Ser Ser Arg Gly
```

-continued

```
            530                 535                 540
tgt gtg gat atc agg gga tct ggt ggg act gat gtg gat cag gct ggg    1680
Cys Val Asp Ile Arg Gly Ser Gly Gly Thr Asp Val Asp Gln Ala Gly
545                 550                 555                 560 aac cag gaa tcc atg gag cat ggt gac tgc caa gat gga gct act ggg    1728
Asn Gln Glu Ser Met Glu His Gly Asp Cys Gln Asp Gly Ala Thr Gly
                565                 570                 575 agt cag tct ggc cct ggg gat tct gct tat ggc gtg cgc cgg gac ctg    1776
Ser Gln Ser Gly Pro Gly Asp Ser Ala Tyr Gly Val Arg Arg Asp Leu
            580                 585                 590 ccc cca gcc tcg gcc tcc cgc tcc gtc ccc atc cca ctc ctc ctg gcc    1824
Pro Pro Ala Ser Ala Ser Arg Ser Val Pro Ile Pro Leu Leu Leu Ala
        595                 600                 605 agt gtg gcc gca gct ttt gcc ctg ggc gcc tca gtc tct ggc ctc ctg    1872
Ser Val Ala Ala Ala Phe Ala Leu Gly Ala Ser Val Ser Gly Leu Leu
    610                 615                 620 gtc tcc tgt gct tgt cgc cgc gcc cac cga cgt cgg ggc aag gac atc    1920
Val Ser Cys Ala Cys Arg Arg Ala His Arg Arg Gly Lys Asp Ile
625                 630                 635                 640 gag act ccc ggg ctc ccg cgc cct ctc tcc ctc cgc agt ttg gcc cgg    1968
Glu Thr Pro Gly Leu Pro Arg Pro Leu Ser Leu Arg Ser Leu Ala Arg
                645                 650                 655 ctc cac ggt ggg ggc cca gag ccc ccg ccc tcc aag gac ggg gac        2016
Leu His Gly Gly Pro Glu Pro Pro Pro Ser Lys Asp Gly Asp
            660                 665                 670 gcg gtg cag acg ccg cag ctc tac acc acc ttc ctg ccg cct ccg gag    2064
Ala Val Gln Thr Pro Gln Leu Tyr Thr Thr Phe Leu Pro Pro Pro Glu
        675                 680                 685 ggc gtg ccc ccg ccg gag ctg gcc tgc ctg ccc acc ccc gag tcc acg    2112
Gly Val Pro Pro Pro Glu Leu Ala Cys Leu Pro Thr Pro Glu Ser Thr
    690                 695                 700 ccg gag ctg ccg gtc aag cac ctc cgc gcc gcc ggg gac ccc tgg gag    2160
Pro Glu Leu Pro Val Lys His Leu Arg Ala Ala Gly Asp Pro Trp Glu
705                 710                 715                 720 tgg aac cag aac agg aac aac gcc aag gag ggt ccg ggc cgc tca cgg    2208
Trp Asn Gln Asn Arg Asn Asn Ala Lys Glu Gly Pro Gly Arg Ser Arg
                725                 730                 735 ggc ggg cac gcg gcg ggc ggg ccc gcg ccc cgc gtg ctg gtg agg cca    2256
Gly Gly His Ala Ala Gly Gly Pro Ala Pro Arg Val Leu Val Arg Pro
            740                 745                 750 ccg ccg ccc ggt tgt ccc ggg cag gcc gtg gaa gtc acc acc ctg gag    2304
Pro Pro Pro Gly Cys Pro Gly Gln Ala Val Glu Val Thr Thr Leu Glu
        755                 760                 765 gaa ctg ctg cgc tac ctg cac ggc ccg cag ccg ccc aga aag ggg gcc    2352
Glu Leu Leu Arg Tyr Leu His Gly Pro Gln Pro Pro Arg Lys Gly Ala
    770                 775                 780 gag ccc ccc gcc cct tta acc tcg cgg gcg ctc ccg ccg gag ccc gcc    2400
Glu Pro Pro Ala Pro Leu Thr Ser Arg Ala Leu Pro Pro Glu Pro Ala
785                 790                 795                 800 ccc gcc ctc ttg ggc ggc ccc agc ccc agg ccc cac gag tgc gcc tcg    2448
Pro Ala Leu Leu Gly Gly Pro Ser Pro Arg Pro His Glu Cys Ala Ser
                805                 810                 815 ccg ctg agg ctg gac gtg ccc ccc gag ggc agg tgc gcc tct gcc ccc    2496
Pro Leu Arg Leu Asp Val Pro Pro Glu Gly Arg Cys Ala Ser Ala Pro
            820                 825                 830 gcc cgg ccc gcg ctc tcc gcc ccc gct ccc cgg ctg ggc gtc ggc gga    2544
Ala Arg Pro Ala Leu Ser Ala Pro Ala Pro Arg Leu Gly Val Gly Gly
        835                 840                 845 ggc cgg agg ttg cct ttc tcc ggc cac cgg gcc ccc cct gcc ctg ctc    2592
```

-continued

```
Gly Arg Arg Leu Pro Phe Ser Gly His Arg Ala Pro Pro Ala Leu Leu
        850                 855                 860 act cga gtc ccc tcg gga ggt ccc tcc agg tac tcc ggg ggt ccc ggg    2640
Thr Arg Val Pro Ser Gly Gly Pro Ser Arg Tyr Ser Gly Gly Pro Gly
865                 870                 875                 880 aag cac ctc ctg tac ctg ggc cgg ccc gag ggc tac cgg ggc cgc gcc    2688
Lys His Leu Leu Tyr Leu Gly Arg Pro Glu Gly Tyr Arg Gly Arg Ala
                885                 890                 895 ctg aaa agg gtg gac gtc gag aag ccc cag ttg tcc ctg aag cct ccc    2736
Leu Lys Arg Val Asp Val Glu Lys Pro Gln Leu Ser Leu Lys Pro Pro
            900                 905                 910 ctc gtc ggg ccc tcc tcc cgc cag gcc gtc ccg aac ggc ggc cgt ttc    2784
Leu Val Gly Pro Ser Ser Arg Gln Ala Val Pro Asn Gly Gly Arg Phe
        915                 920                 925 aac ttt                                                             2790
Asn Phe
    930
```

<210> SEQ ID NO 6
<211> LENGTH: 930
<212> TYPE: PRT
<213> ORGANISM: Homo sapiens
<220> FEATURE:
<221> NAME/KEY: misc_feature
<222> LOCATION: ()..()
<223> OTHER INFORMATION: Tissue Type: Child Brain
<221> NAME/KEY: misc_feature
<222> LOCATION: ()..()
<223> OTHER INFORMATION: Identification Method: P for resulting peptide

<400> SEQUENCE: 6

```
Met Pro Arg Ala Pro His Phe Met Pro Leu Leu Leu Leu Leu Leu Leu
1               5                   10                  15

Leu Ser Leu Pro His Thr Gln Ala Ala Phe Pro Gln Asp Pro Leu Pro
                20                  25                  30

Leu Leu Ile Ser Asp Leu Gln Gly Thr Ser Pro Leu Ser Trp Phe Arg
            35                  40                  45

Gly Leu Glu Asp Asp Ala Val Ala Ala Glu Leu Gly Leu Asp Phe Gln
        50                  55                  60

Arg Phe Leu Thr Leu Asn Arg Thr Leu Leu Val Ala Ala Arg Asp His
65                  70                  75                  80

Val Phe Ser Phe Asp Leu Gln Ala Glu Glu Gly Glu Gly Leu Val
                85                  90                  95

Pro Asn Lys Tyr Leu Thr Trp Arg Ser Gln Asp Val Glu Asn Cys Ala
                100                 105                 110

Val Arg Gly Lys Leu Thr Asp Glu Cys Tyr Asn Tyr Ile Arg Val Leu
            115                 120                 125

Val Pro Trp Asp Ser Gln Thr Leu Leu Ala Cys Gly Thr Asn Ser Phe
        130                 135                 140

Ser Pro Val Cys Arg Ser Tyr Gly Ile Thr Ser Leu Gln Gln Glu Gly
145                 150                 155                 160

Glu Glu Leu Ser Gly Gln Ala Arg Cys Pro Phe Asp Ala Thr Gln Ser
                165                 170                 175

Asn Val Ala Ile Phe Ala Glu Gly Ser Leu Tyr Ser Ala Thr Ala Ala
            180                 185                 190

Asp Phe Gln Ala Ser Asp Ala Val Val Tyr Arg Ser Leu Gly Pro Gln
        195                 200                 205

Pro Pro Leu Arg Ser Ala Lys Tyr Asp Ser Lys Trp Leu Arg Glu Pro
    210                 215                 220
```

-continued

```
His Phe Val Gln Ala Leu Glu His Gly Asp His Val Tyr Phe Phe Phe
225                 230                 235                 240

Arg Glu Val Ser Val Glu Asp Ala Arg Leu Gly Lys Val Gln Phe Ser
            245                 250                 255

Arg Val Ala Arg Val Cys Lys Arg Asp Met Gly Gly Ser Pro Arg Ala
            260                 265                 270

Leu Asp Arg His Trp Thr Ser Phe Leu Lys Leu Arg Leu Asn Cys Ser
            275                 280                 285

Val Pro Gly Asp Ser Thr Phe Tyr Phe Asp Val Leu Gln Ala Leu Thr
        290                 295                 300

Gly Pro Val Asn Leu His Gly Arg Ser Ala Leu Phe Gly Val Phe Thr
305                 310                 315                 320

Thr Gln Thr Asn Ser Ile Pro Gly Ser Ala Val Cys Ala Phe Tyr Leu
                325                 330                 335

Asp Glu Ile Glu Arg Gly Phe Glu Gly Lys Phe Lys Glu Gln Arg Ser
            340                 345                 350

Leu Asp Gly Ala Trp Thr Pro Val Ser Glu Asp Arg Val Pro Ser Pro
        355                 360                 365

Arg Pro Gly Ser Cys Ala Gly Val Gly Ala Ala Leu Phe Ser Ser
370                 375                 380

Ser Arg Asp Leu Pro Asp Asp Val Leu Thr Phe Ile Lys Ala His Pro
385                 390                 395                 400

Leu Leu Asp Pro Ala Val Pro Pro Val Thr His Gln Pro Leu Leu Thr
                405                 410                 415

Leu Thr Ser Arg Ala Leu Leu Thr Gln Val Ala Val Asp Gly Met Ala
            420                 425                 430

Gly Pro His Ser Asn Ile Thr Val Met Phe Leu Gly Ser Asn Asp Gly
            435                 440                 445

Thr Val Leu Lys Val Leu Thr Pro Gly Gly Arg Ser Gly Gly Pro Glu
    450                 455                 460

Pro Ile Leu Leu Glu Glu Ile Asp Ala Tyr Ser Pro Ala Arg Cys Ser
465                 470                 475                 480

Gly Lys Arg Thr Ala Gln Thr Ala Arg Arg Ile Ile Gly Leu Glu Leu
            485                 490                 495

Asp Thr Glu Gly His Arg Leu Phe Val Ala Phe Ser Gly Cys Ile Val
            500                 505                 510

Tyr Leu Pro Leu Ser Arg Cys Ala Arg His Gly Ala Cys Gln Arg Ser
        515                 520                 525

Cys Leu Ala Ser Gln Asp Pro Tyr Cys Gly Trp His Ser Ser Arg Gly
530                 535                 540

Cys Val Asp Ile Arg Gly Ser Gly Thr Asp Val Asp Gln Ala Gly
545                 550                 555                 560

Asn Gln Glu Ser Met Glu His Gly Asp Cys Gln Asp Gly Ala Thr Gly
                565                 570                 575

Ser Gln Ser Gly Pro Gly Asp Ser Ala Tyr Gly Val Arg Arg Asp Leu
            580                 585                 590

Pro Pro Ala Ser Ala Ser Arg Ser Val Pro Ile Pro Leu Leu Leu Ala
        595                 600                 605

Ser Val Ala Ala Ala Phe Ala Leu Gly Ala Ser Val Ser Gly Leu Leu
    610                 615                 620

Val Ser Cys Ala Cys Arg Arg Ala His Arg Arg Gly Lys Asp Ile
625                 630                 635                 640
```

-continued

```
Glu Thr Pro Gly Leu Pro Arg Pro Leu Ser Leu Arg Ser Leu Ala Arg
            645                 650                 655
Leu His Gly Gly Gly Pro Glu Pro Pro Pro Ser Lys Asp Gly Asp
    660                 665                 670
Ala Val Gln Thr Pro Gln Leu Tyr Thr Thr Phe Leu Pro Pro Glu
        675                 680                 685
Gly Val Pro Pro Glu Leu Ala Cys Leu Pro Thr Pro Glu Ser Thr
    690                 695                 700
Pro Glu Leu Pro Val Lys His Leu Arg Ala Ala Gly Asp Pro Trp Glu
705                 710                 715                 720
Trp Asn Gln Asn Arg Asn Asn Ala Lys Glu Gly Pro Gly Arg Ser Arg
                725                 730                 735
Gly Gly His Ala Ala Gly Pro Ala Pro Arg Val Leu Val Arg Pro
            740                 745                 750
Pro Pro Pro Gly Cys Pro Gly Gln Ala Val Glu Val Thr Thr Leu Glu
            755                 760                 765
Glu Leu Leu Arg Tyr Leu His Gly Pro Gln Pro Pro Arg Lys Gly Ala
    770                 775                 780
Glu Pro Pro Ala Pro Leu Thr Ser Arg Ala Leu Pro Pro Glu Pro Ala
785                 790                 795                 800
Pro Ala Leu Leu Gly Gly Pro Ser Pro Arg Pro His Glu Cys Ala Ser
                805                 810                 815
Pro Leu Arg Leu Asp Val Pro Glu Gly Arg Cys Ala Ser Ala Pro
            820                 825                 830
Ala Arg Pro Ala Leu Ser Ala Pro Ala Arg Leu Gly Val Gly Gly
        835                 840                 845
Gly Arg Arg Leu Pro Phe Ser Gly His Arg Ala Pro Pro Ala Leu Leu
850                 855                 860
Thr Arg Val Pro Ser Gly Gly Pro Ser Arg Tyr Ser Gly Gly Pro Gly
865                 870                 875                 880
Lys His Leu Leu Tyr Leu Gly Arg Pro Glu Gly Tyr Arg Gly Arg Ala
                885                 890                 895
Leu Lys Arg Val Asp Val Glu Lys Pro Gln Leu Ser Leu Lys Pro Pro
            900                 905                 910
Leu Val Gly Pro Ser Ser Arg Gln Ala Val Pro Asn Gly Gly Arg Phe
        915                 920                 925
Asn Phe
    930

<210> SEQ ID NO 7
<211> LENGTH: 170
<212> TYPE: DNA
<213> ORGANISM: Homo sapiens
<220> FEATURE:
<221> NAME/KEY: misc_feature
<222> LOCATION: ()..()
<223> OTHER INFORMATION: Tissue Type: Brain
<221> NAME/KEY: misc_feature
<222> LOCATION: (1)..(170)
<223> OTHER INFORMATION: CDS; Identification Method: E
<221> NAME/KEY: misc_feature
<222> LOCATION: (155)..(155)
<223> OTHER INFORMATION: "n" at position 155 is a, g, c, t/u, unknown,
      or other

<400> SEQUENCE: 7
tggctgtatt gtctacctcc ctctcagccg gtgtgcccgg catggggcct gtcagaggag      60
ctgtttggct tctcaggacc catactgtgg atggcatagc tccaggggct gtgtggatat     120
``` cagggatct ggtgggactg atgtggatca ggctnggaac caggaatcca                    170

<210> SEQ ID NO 8
<211> LENGTH: 18
<212> TYPE: DNA
<213> ORGANISM: Synthetic DNA
<220> FEATURE:
<221> NAME/KEY: misc_feature
<222> LOCATION: (1)..(18)
<223> OTHER INFORMATION: CDS; Identification Method: P

<400> SEQUENCE: 8
tggctgtatt gtctacct                                                      18

<210> SEQ ID NO 9
<211> LENGTH: 20
<212> TYPE: DNA
<213> ORGANISM: Synthetic DNA
<220> FEATURE:
<221> NAME/KEY: misc_feature
<222> LOCATION: (1)..(20)
<223> OTHER INFORMATION: CDS; Identification Method: P
<221> NAME/KEY: misc_feature
<222> LOCATION: (16)..(16)
<223> OTHER INFORMATION: "n" at position 16 is a, g, c, t/u, unknown,
      or other

<400> SEQUENCE: 9
tggattcctg gttccnagcc                                                    20

<210> SEQ ID NO 10
<211> LENGTH: 18
<212> TYPE: DNA
<213> ORGANISM: Synthetic DNA
<220> FEATURE:
<221> NAME/KEY: misc_feature
<222> LOCATION: (1)..(18)
<223> OTHER INFORMATION: CDS; Identification Method: E

<400> SEQUENCE: 10
tgtgtaaacg tgacatgg                                                      18

<210> SEQ ID NO 11
<211> LENGTH: 18
<212> TYPE: DNA
<213> ORGANISM: Synthetic DNA
<220> FEATURE:
<221> NAME/KEY: misc_feature
<222> LOCATION: (1)..(18)
<223> OTHER INFORMATION: CDS; Identification Method: E

<400> SEQUENCE: 11
tgctagtcag agtgagga                                                      18

<210> SEQ ID NO 12
<211> LENGTH: 7
<212> TYPE: PRT
<213> ORGANISM: Homo sapiens
<220> FEATURE:
<221> NAME/KEY: misc_feature
<222> LOCATION: (1)..(1)
<223> OTHER INFORMATION: First "Xaa" is Gln or Arg
<221> NAME/KEY: misc_feature
<222> LOCATION: (6)..(6)
<223> OTHER INFORMATION: Second "Xaa" is Ala or Gly

<400> SEQUENCE: 12

Xaa Asp Pro Tyr Cys Xaa Trp

```
1               5

<210> SEQ ID NO 13
<211> LENGTH: 14
<212> TYPE: PRT
<213> ORGANISM: Unknown
<220> FEATURE:
<221> NAME/KEY: misc_feature
<222> LOCATION: ()..()
<223> OTHER INFORMATION: Description of Unknown Organism: Myc tag

<400> SEQUENCE: 13

Asp Ile Gly Gly Glu Gln Lys Leu Ile Ser Glu Glu Asp Leu
1               5                   10
```